(12) United States Patent
Ferrara et al.

(10) Patent No.: US 6,371,917 B1
(45) Date of Patent: Apr. 16, 2002

(54) ULTRASOUND BUBBLE RECOGNITION IMAGING

(75) Inventors: Katherine W. Ferrara, Davis, CA (US); Karen Elizabeth Morgan, Charlottesville, VA (US); Paul Dayton, Davis, CA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/485,412
(22) PCT Filed: Sep. 17, 1998
(86) PCT No.: PCT/US98/87182
§ 371 Date: Aug. 31, 2000
§ 102(e) Date: Aug. 31, 2000
(87) PCT Pub. No.: WO99/17808
PCT Pub. Date: Apr. 15, 1999

Related U.S. Application Data

(60) Provisional application No. 60/060,790, filed on Oct. 3, 1997, and provisional application No. 60/071,389, filed on Jan. 15, 1998.

(51) Int. Cl.$^7$ .................................................. A61B 8/14
(52) U.S. Cl. ........................................................ 600/458
(58) Field of Search ................................. 600/437, 441, 600/443, 458; 424/9.51, 9.52, 9.35; 514/180

(56) References Cited

U.S. PATENT DOCUMENTS 5,706,819 A * 1/1998 Hwang et al. ............... 600/458

* cited by examiner

*Primary Examiner*—Marvin M. Lateef
*Assistant Examiner*—Ali M. Imam
(74) *Attorney, Agent, or Firm*—Robert J. Decker

(57) ABSTRACT

In a method of identifying gaseous bubbles in a liquid, an ultrasound contrast agent is introduced into the liquid so as to form gaseous bubbles in the liquid. A first ultrasound pulse centered at a first frequency is directed onto the bubbles so as to cause the bubbles to undergo a first oscillating size change and produce a first oscillating echo signal corresponding thereto. The first oscillating echo signal produced by the bubbles is detected, and the bubbles are identified based upon the detected first echo signal.

38 Claims, 22 Drawing Sheets

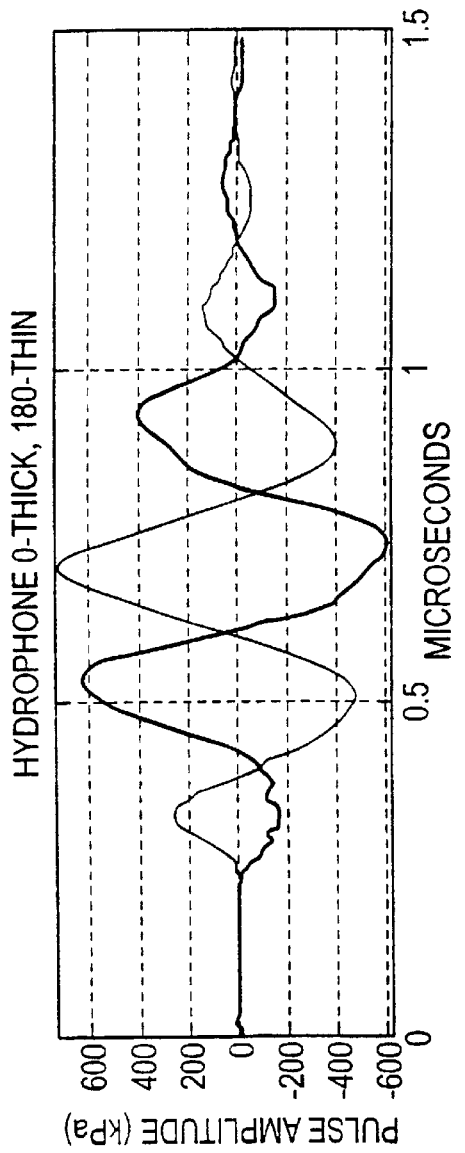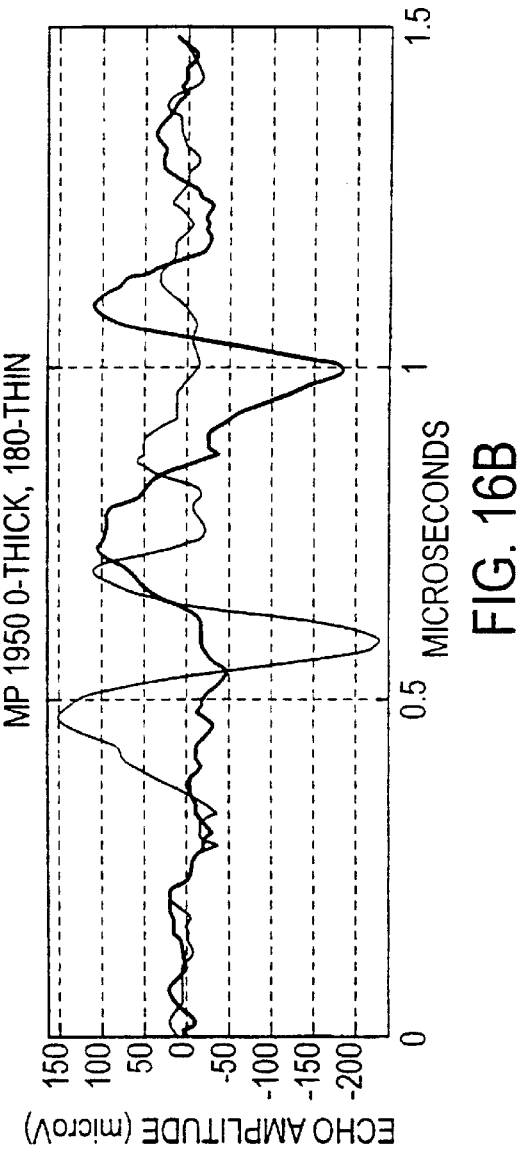

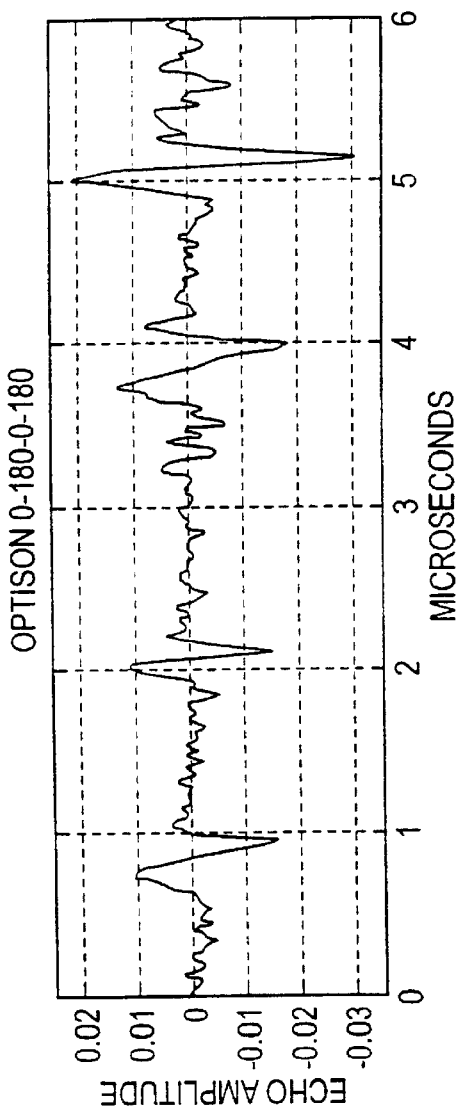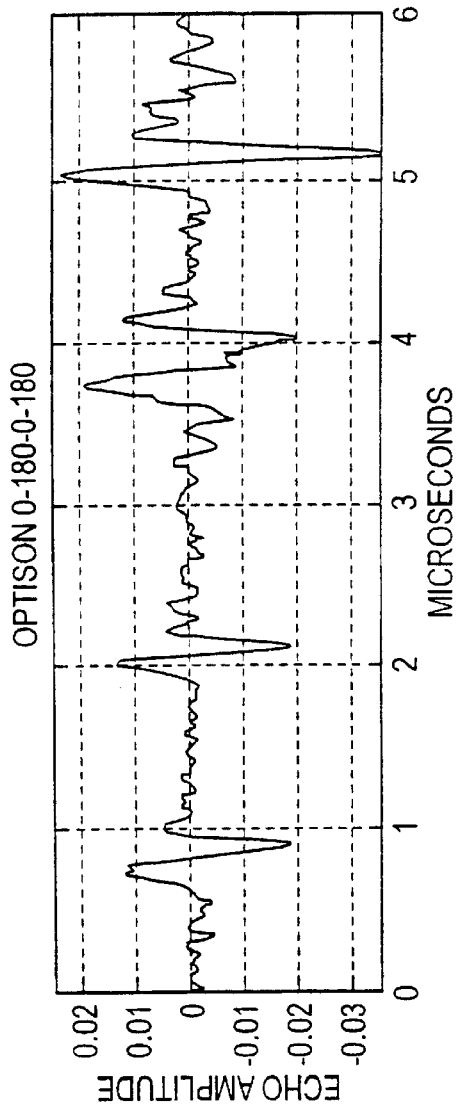

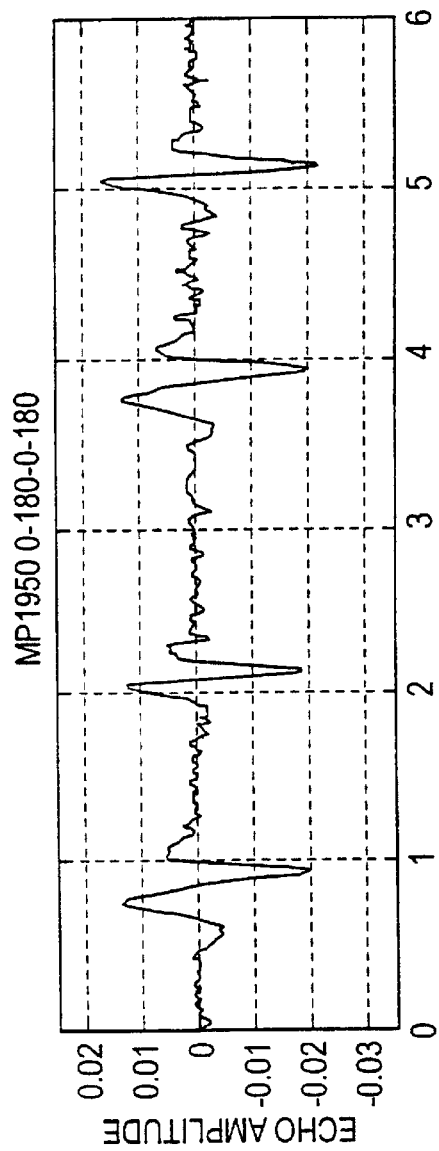
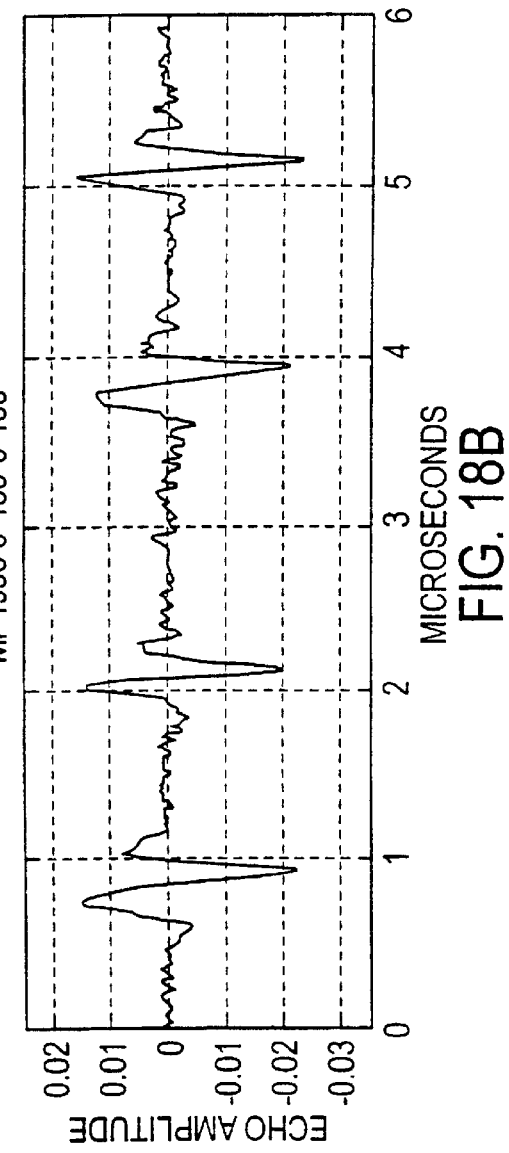

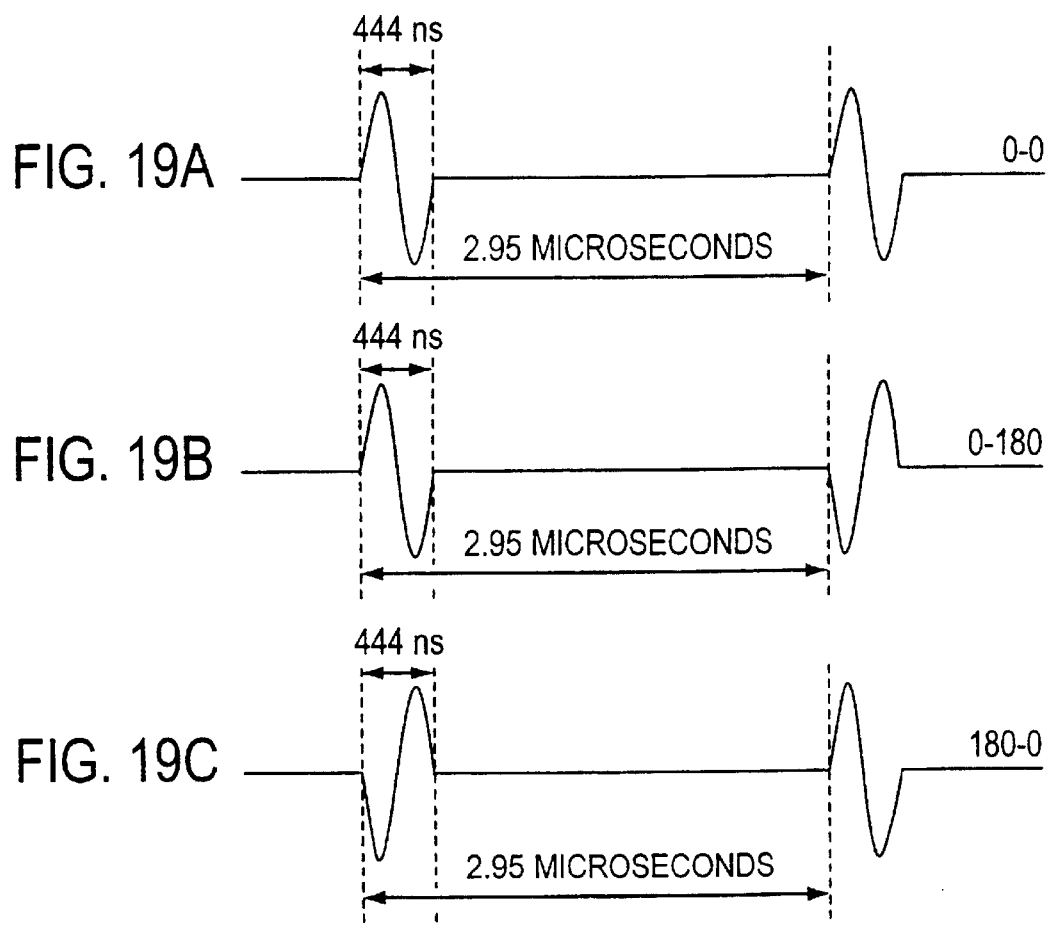

ULTRASOUND BUBBLE RECOGNITION IMAGING

This Appln is a 371 of PCT/U.S.98/18245 filed Sep. 17, 1998, which claims benefit of Prov No. 60/060,790 filed Oct. 3, 1997 which claims benefit of Prov. No. 60/071,389 Jan. 15, 1998.

BACKGROUND OF THE INVENTION

1. Field of the Invention

The present invention relates to the field of ultrasound contrast agents.

2. Description of the Background Art

Physicians and physiologists have long recognized the significance of local perfusion in the assessment of wound healing, diabetes, viability of transplanted organs and reattached limbs, the diagnosis of cancerous lesions and the assessment of myocardial function, however to date there is no method that can provide a direct assessment. It has been clear that fundamental changes in tissue perfusion are involved in disease progression, or in some cases in the onset of a disease state. Many imaging techniques have been developed to indirectly detect ischemia, for example ultrasonic and magnetic resonance schemes that evaluate the extent and quality of the regional motion of the beating heart. An opportunity is presented by contrast-assisted ultrasonic imaging with second and third generation agents and new imaging strategies, since the echoes from blood are now far stronger, and local bubble destruction may allow us to map microvascular transit time on a far smaller scale. In addition, we may have the ability to remotely manipulate agents within the body using radiation force. Contrast-assisted imaging is also less expensive than alternative vascular imaging techniques.

Contrast-assisted imaging methods have failed to produce the expected results for reasons that include the lack if fundamental understanding of the interaction between ultrasound and the microbubbles, and difficulties associated with some of the artifacts that can arise. In cardiology, the use of the returned signal amplitude has been particularly difficult since the contrast agent can also attenuate the signal and therefore make interpretation of amplitude fluctuations difficult.

Cancer currently accounts for 15.8% of the deaths within the United States. Although malignant breast masses can often be differentiated using ultrasound due to an increase in the attenuation and decrease in the backscattered echo, these changes are absent in approximately 10% of malignant masses.

More than 60 million people in the United States have some form of cardiovascular disease, with CVD playing a major role in more than 954,000 deaths annually. This is more than 42 percent of the deaths in the United States each year. Ultrasound remains the premier imaging modality for the detection and valuation of CVD, however the current inability of ultrasound to map flow within the coronary arteries, or to map myocardial perfusion is a significant limitation. Ultrasound contrast imaging shows the potential to address these current limitations but needs improved signal processing with definitive detection of bubbles to improve clinical acceptance.

While ultrasonic contrast agents were first considered in 1968, the development of agents with extended persistence provides exciting new opportunities to image the microvasculature. In the past few years, microbubbles have been developed that can survive within the circulation for extended periods. New agents include high molecular weight gases that have a low diffusion constant and have been incorporated into lipid or albumin shells. Agents under development include substances that are intended to adhere to particular tissues and improve the detection of plaque or tumor vasculature.

Also, while contrast agents have been used to increase the amplitude of scatter since 1970, techniques to differentiate bubble and tissue echoes have been proposed very recently. The scattering and attenuation properties of certain contrast agents have been studied. Experiments have shown the nonlinear increase in scattered echoes and the change in harmonic signal content with transmitted pressure. Use of harmonic imaging in vitro has been demonstrated and has provided evidence that cross correlation can be used to track microbubbles. Use of 5 MHz transmission and 2.5 MHz subharmonic reception has been evaluated, demonstrating that subharmonic peaks from the contrast agent Albunex® can be detected in vitro. Studies of attenuation and transmission have shown the high attenuation of acoustic contrast agents, a significant factor in cardiac imaging. New agents have been presented in many recent conference abstracts.

Clinical evaluation of current contrast-assisted imaging techniques have shown that artifacts can reduce the effectiveness of estimations of myocardial perfusion. Specifically, attenuation and rib artifacts are problematic for operating modes which base the perfusion estimate on the video intensity of the returned signal to map perfusion. Concerns about safety have been reported in, particularly for high intensities and low frequencies (<2 MHz). There remains the need in the art for improved ultrasound techniques.

SUMMARY OF THE INVENTION

In accordance with the present invention, a method of identifying gaseous bubbles in a liquid comprises introducing an ultrasound contrast agent into the liquid so as to form gaseous bubbles in the liquid. A first ultrasound pulse centered at a first frequency is directed onto the bubbles, so as to cause the bubbles to undergo a first oscillating size change and produce a corresponding first oscillating echo signal. The first oscillating echo signal produced by the bubbles is detected, and the bubbles are identified based upon the detected first echo signal.

BRIEF DESCRIPTION OF THE DRAWINGS

FIGS. 16a and 16b graphically depict pulse amplitude and echo amplitude of a hydrophone recording of transmitted signals in 0° and 180° cases.

FIGS. 17a and 17b graphically depict two sets of recordings of echoes from four pulses separated by 1.25 microseconds, generated by a single albumin-shelled bubble.

FIGS. 18a and 18b graphically depict two sets of recordings of echoes from four pulses separated by 1.25 microseconds, generated by a single lipid-shelled bubble.

FIGS. 19a, 19b and 19c graphically depict sets of transmitted signals used to excite a wideband transducer, from lipid-shelled bubbles having a perfluorohydrocarbon core.

DETAILED DESCRIPTION OF THE INVENTION

Figure 1:
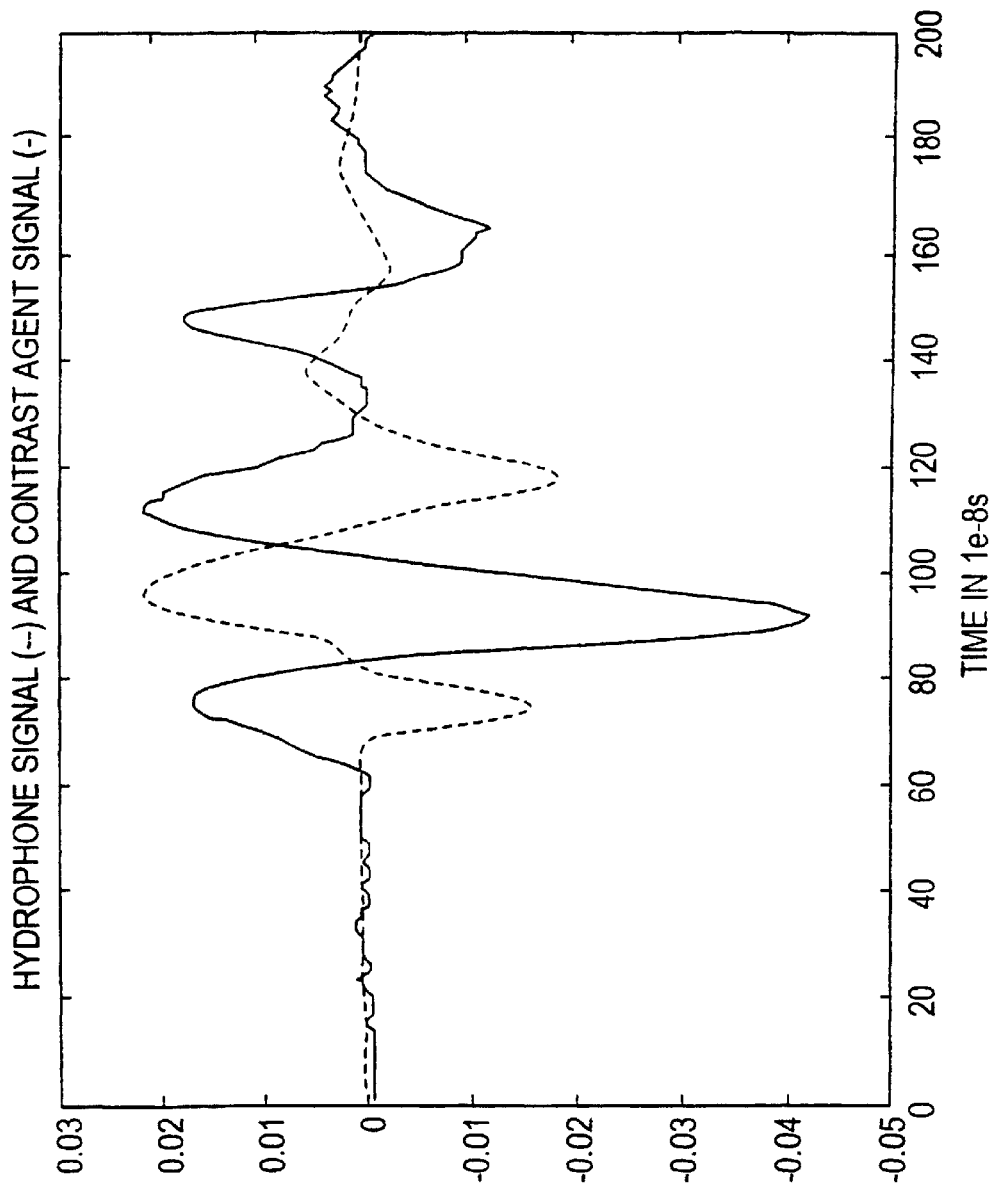
FIG. 1 is a graph showing hydrophone recording from a transmitted signal and a contrast agent echo from this signal.

According to the present invention, ultrasound contrast agents produce unique echoes that can be differentiated from the surrounding tissue using, e.g., time domain recognition techniques. Recognition of these echoes facilitates robust contrast-assisted ultrasound imaging.

In addition, it has been discovered that the echo from an ultrasonic contrast agent is produced by pairs of transmitted rarefactional and compressional cycles, and that a pair of half cycles in the order (rarefaction-compression) produces a strong echo. Thus, transmission strategies that vary the order and number of half cycles as well as their strength and frequency can be used in differentiating contrast agents from tissue. Bubbles and tissue produce higher order frequency terms when the bubble is insonified at the bubble's resonant frequency. Shelled bubbles do not respond to an initial half-cycle of acoustic compression, but rather require the expansion produced by rarefaction to proceed compression.

The invention eliminates many of the problems that have limited the usefulness of ultrasound contrast agents. Specifically, the invention is robust in the presence of intervening attenuation, tissue motion, and bubble destruction.

The invention allows for the use of wideband signal transmission which greatly improves spatial resolution in comparison with the narrowband transmission strategies required for harmonic imaging methods. Wideband signal transmission produces echoes with an intensity equal to or greater than with narrowband signal transmission. For second-generation contract agents, the spatial resolution achieved with wideband insonation and higher frequency insonation is superior to narrowband or lower frequency techniques.

Suitable contract agents contain a gas. The gas may be any suitable gas such as air, or preferably a high molecular weight gas. Preferred aspects of the present invention rely on the compressibility of the resulting bubble, with preferred compressibility being about $5 \times 10^{-7}$ $m^2/N$ or greater. Examples of suitable agents include the commercial products of Albunex® and Optison® from Mallinckrodt, Inc. and Molecular Biosystems, Inc., both of which have a gas core and albumin shell, the gas core being respectfully air or perfluoropropane.

The bubble shell may be any suitable material, such as protein, lipid or other material.

A range of suitable bubble diameters can be about 1–12 microns, e.g., about 2 microns.

Suitable in vivo bubble durations can be about 10–60 minutes, e.g., about 20 minutes.

The resonant frequency of a bubble typically is determined by finding the frequency at which attenuation and backscatter of the echo is greatest. The resonant frequencies of typical bubbles are about 1.5–5 MHz.

In order to recognize a bubble signal, the invention can be applied as follows.

Generation of the required echo or echoes can be accomplished by injection of a suitable ultrasound contrast agent and transmission of a short (wideband) ultrasound pulse at the resonant frequency of the bubbles. A typical "short" pulse is about three cycles of the center frequency or less. A preferred length is about 1.5 cycles. The bandwidth of this pulse for a center frequency of about 2 MHz is about 0.6 MHz or greater, and a center frequency of 5 MHz is approximately 1.6 MHz.

In order to improve identification of the bubble, the initial transmission can be followed with other pulses, for which the order of compression and rarefaction, the number of rarefaction or compressional cycles, or the intensity of the compressional and rarefactional cycles, has been altered. A preferred signal is about a 1.5 cycle transmission. One method of incorporating multiple pulses is to transmit this signal with one rarefactional, one compressional and then one rarefactional cycle; then change the order of excitation such that the signal contains one compressional, one rarefactional, then one compressional cycle. The two resulting echoes (E1 and E2) are then processed as discussed below.

The bubble can be recognized by any of several signal processing embodiments. Several begin by correlating the echo signal with a bubble identifier, an example of which is shown in FIG. 1 for an exemplary contrast agent, excited at 2 MHz. The bubble identifier, a reference echo signal indicative of the bubbles of a particular contrast agent, is obtained by recording the echo from a single bubble for a specific set of imaging parameters. Thus, for a specific transmitted intensity (e.g., 1 MPa), a specific transmitted pulse (e.g., 1.5 cycles), and a specific center frequency (e.g., 2 or 5 MHz), a bubble identifier is recorded for each contrast agent.

Additional certainty can then be obtained by incorporating the information from a second frequency. In order to incorporate the frequency information, the two echoes from two transmission frequencies are processed by correlating the signal with the bubble identifiers as described. Transmission at the resonant frequency of the bubble is performed after transmission at the second frequency, reducing the chance of breaking the bubble. Boolean logic is used to determine whether the bubble was found at either or both frequencies. The two frequencies are chosen to be the resonant frequency and a frequency above or below this frequency. For a contrast agent having a resonant frequency of about 5 MHz, the second frequency could be about 2 MHz or about 9 MHz, depending on the depth of the region to be imaged. In each case the bubble identifier is recorded as discussed above. For a superficial region of interest 9 MHz could be chosen as the second frequency. For a deep target, 2 MHz could be chosen.

Thus, echo E1 obtained with 2 MHz transmission is correlated with the bubble identifier recorded for 2 MHz transmission. Echo E2, obtained with 5 MHz transmission, would be correlated with the bubble identifier recorded for 5 MHz transmission. A bubble is identified if the correlation at each frequency (normalized by the transmitted power) exceeds a preselected threshold.

Additional certainty of bubble discovery can also be obtained by incorporating the information from additional pulses. The additional transmitted pulses as noted above can utilize a different number of order of compressional and rarefactional cycles, or the bubble echo, in a predictable manner. This change in the transmitted pulse can be small, and can significantly change the echo from bubbles, but not from the surrounding tissue. A preferred set of transmitted pulses will change the echo from the bubble with a minimal change in the echo from a stationary target (tissue) that surrounds the bubble. One example described above involves changing the order of compressional and rarefactional cycles. A small change in the transmitted amplitude can also accomplish this. For example, a signal with a small compressional and large rarefactional half-cycle can be transmitted, followed by the reverse, with the change in amplitude on the order of a factor of two. Reversing the order of transmission of the half cycles produces an extra half cycle in the received signal.

The resulting echoes are then correlated with the appropriate bubble identifier (or prototype) for that particular transmitted pulse. The correlated results are shifted in time as necessary to match the delay of the first transmission. For the example of changing the order of compressional and rarefactional cycles, the pulses are delayed, such that the echo received from the mid-point of the pulse in each case is aligned.

Alternatively, the echoes from the first pulse and later pulses can be summed on a point by point basis, after any relative delay in transmission is removed, by delaying the echo appropriately. The result is greatly increased in the presence of a bubble, thereby removing tissue echoes.

Figure 11:
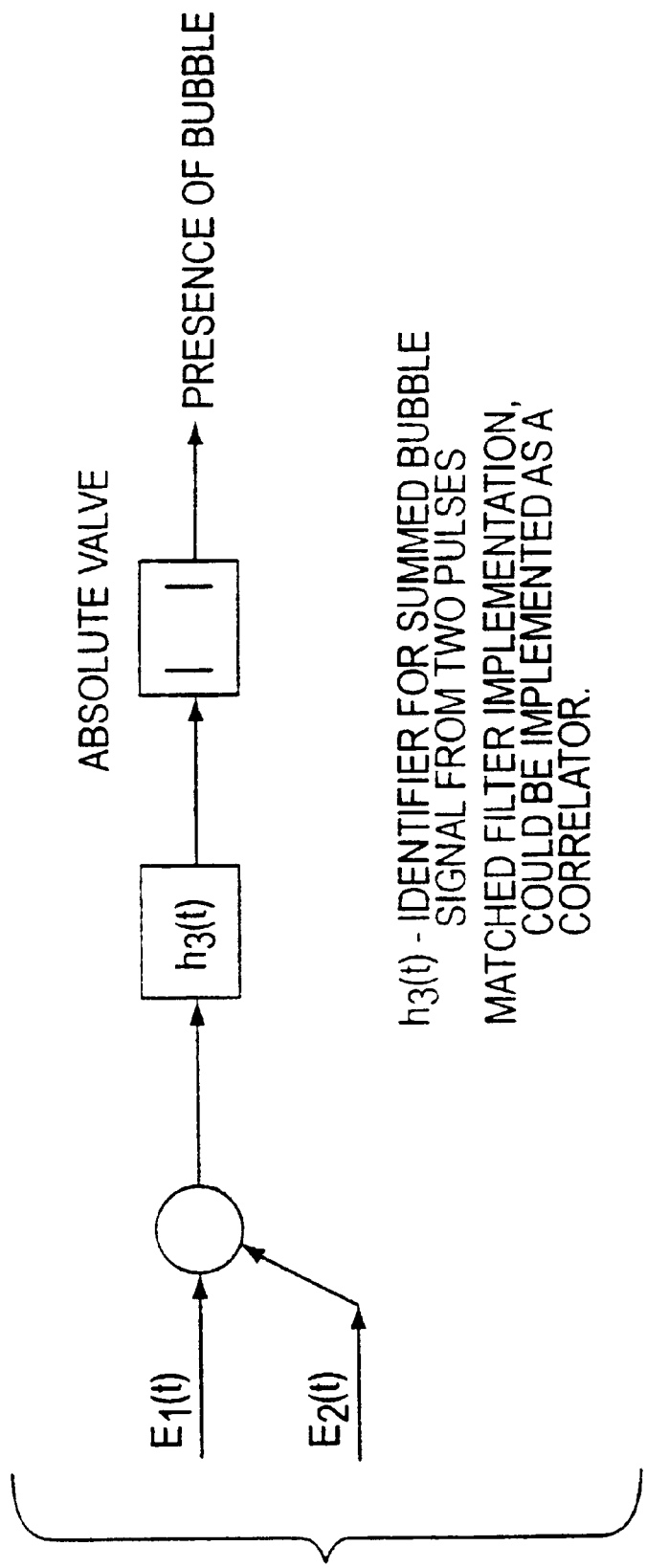
FIG. 11 is a block diagram showing an alternate method in accordance with one embodiment of the present invention.

For example, by changing the order of compressional and rarefactional cycles, the pulses are delayed such that the echo received from the mid-point of the pulse in each case is aligned. The result of the sum can then be correlated with a bubble identifier (FIG. 11).

Figure 12:
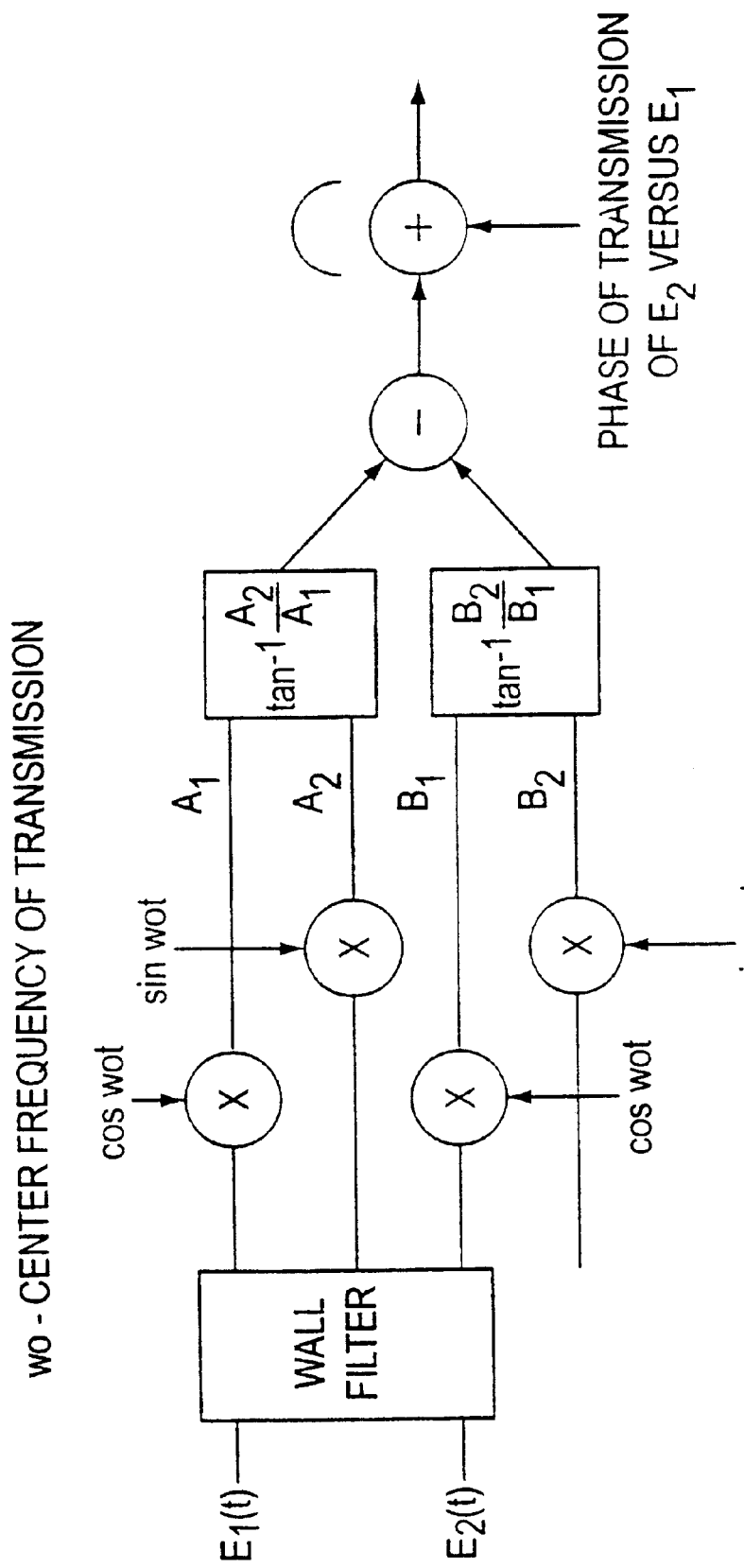
FIG. 12 is a block diagram showing computation of phase of echoes as a function of depth.

Another method is to compute the phase of each echo as a function of depth. The phase of pairs of echoes is then subtracted as a function of depth. Bubbles are then detected at depths where the relative phase between pulses E1(t) and E2(t) is not equivalent to the difference between the transmitted phase at the two depths. This embodiment does not require recognition of the bubble envelope and is shown in FIG. 12. A wall filter may precede this processing. This is a high pass filter, well known in ultrasound signal processing. In this case a set of 4–16 echoes with the characteristics of E1 are acquired. The E1 array and the E2 arrays are passed through the high pass (wall) filter prior to the phase subtraction. The preferred pulse is described above, with 1.5 cycles, but varying in the order of compressional and rarefactional half-cycles would generate E1(t) and E2(t).

Figure 13:
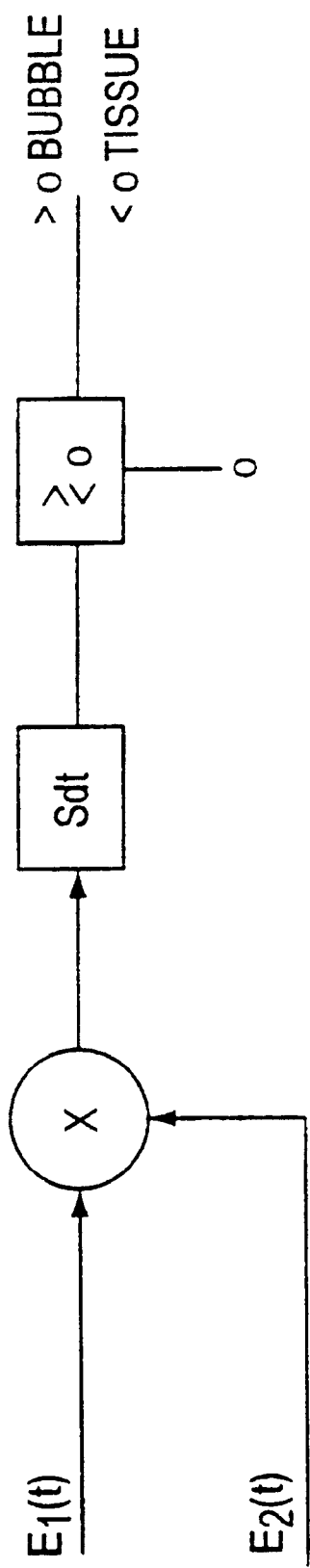
FIG. 13 is a block diagram showing cross-correlation of signals.
Figure 14A:
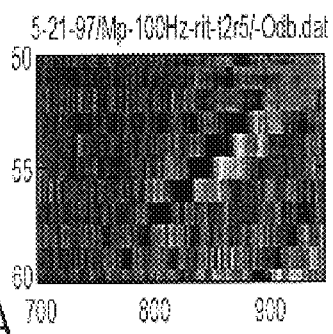
FIG. 14 graphically depicts M-mode and A-lines corresponding to a bubble contrast agent in accordance with the present invention.
Figure 14B:
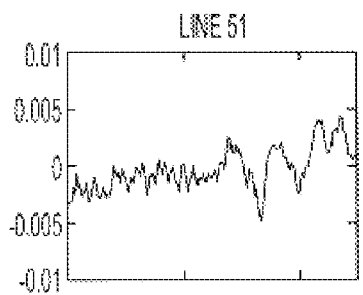
Figure 14C:
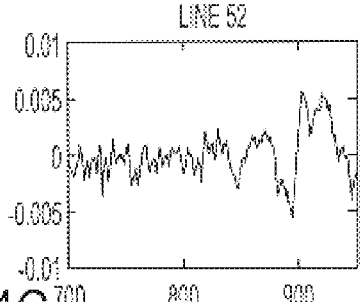
Figure 14D:
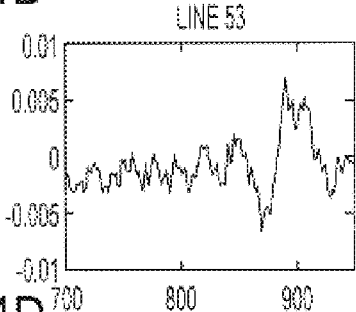
Figure 14E:
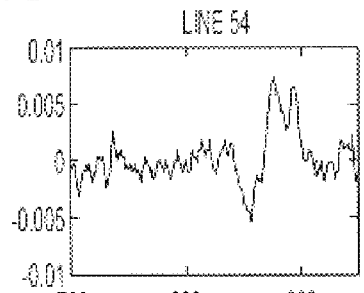
Figure 14F:
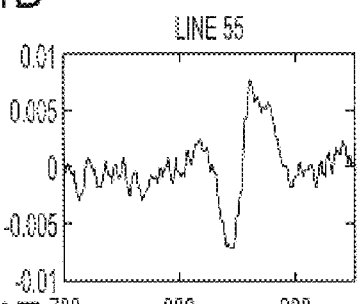
Figure 14G:
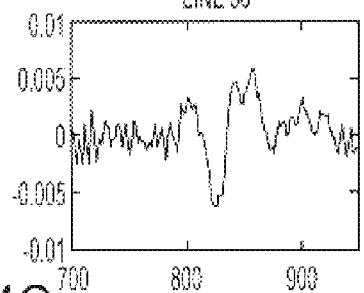
Figure 14H:
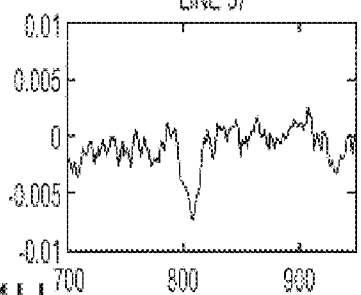
Figure 14I:
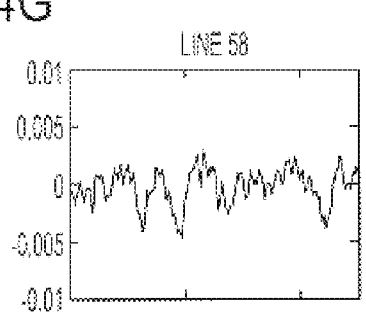

Still another method is to cross-correlate the signals E1(t) and E2(t) at lag 0 on a point by point basis. Thus, echoes from tissue would demonstrate a negative correlation, echoes from bubbles would demonstrate a positive correlation, with the magnitude of this correlation demonstrating the certainty of detection of a bubble (FIG. 13).

As indicated above, the present invention provides a unique bubble echo (not a bubble breaking echo) though the transmission of a short pulse of ultrasound. The bubble echo is unique (different from that produced by tissue) and changes in a unique manner with a shift in the transmitted center frequency, or a change in the transmitted waveform. The unique features include a consistent phase, and height of positive and negative half cycles. The first half cycle in the bubble echo appears to be consistently a positive voltage, corresponding to the bubble expanding. The first half cycle appears to be about ⅓ to ½ of the size of second half cycle, for a 1.5 cycle transmitted pulse. In most cases the third half-cycle contains two rectified harmonics, as shown in FIG. 1.

The present invention provides recognition of detection of these echoes specifically from bubbles based on a unique time-domain signature.

A signal detector can be utilized to recognize a bubble echo using a matched filter, a maximum-likelihood detector, a cross correlation detector, and/or an estimator based on the specific known (non-linear) physical response of the particular type of bubble.

The difference between echo-responses to multiple frequency excitations can be utilized to identify unique echoes from bubbles. This does not require "harmonic" signal processing or non-linear properties.

The unique echo-responses to multiple transmitted signals with varying combinations of compressional and rarefactional cycles can be utilized to recognize a bubble echo. This does not require harmonic signal processing, can take several forms, and does not depend on the "non-linear" properties of bubbles.

One method for this processing is to compute the phase of each echo as a function of depth. The phase of pairs of echoes are then compared as a function of depth. Bubbles are then detected at depths where the relative phase between successive pulses is not equivalent to the difference between the transmitted phase at the two depths. This aspect does not require recognition of the bubble envelope.

In another method, the echoes from successive pulses, with differing numbers, order and amplitude of compressional and rarefactional cycles, are added, yielding a higher value at the location of each bubble.

Recognition and/or rejection of tissue echoes can be based on the use of a bubble recognition scheme to identify those tissues from bubbles utilizing a matched filter, a maximum-likelihood detector, cross correlation detector, and/or an estimator based on the specific known (non-linear) physical response of the particular type of bubble.

Recognition and/or rejection of tissue echoes also can be based on the transmission of multiple pulses with a different number or order of compressional and rarefactional half-cycles with subsequent processing of the received echoes, to reject tissue echoes or to recognize tissue echoes.

One method for this processing is to compute the phase of each echo as a function of depth. The phase of pairs of echoes are then compared as a function of depth. Bubbles are then detected at depths where the relative phase between successive pulses is not equivalent to the difference between the transmitted phases.

Another method is to align the signal and then subtract the echoes on a point by point basis.

The transmission of multiple frequencies can be used to improve the recognition of bubble echoes. Echoes from these multiple transmitted frequencies are then combined. One method of combination would involve the use of a matched filter to recognize the bubble echo at each frequency, followed by the combination of the two filtered signals.

The invention will be further described with reference to the following Figures, which are not intended to be limiting.

FIG. 1 shows Hydrophone recording from transmitted signal and contrast agent echo from this signal. FIG. 1 demonstrates the unique echo following wideband high intensity insonation of a contrast agent bubble. One and one-half cycles of the 2 MHz center frequency were transmitted, and we then listen for the returned echo. The transmitted signal contains a rarefactional, compressional, then rarefactional phase. The returned echo contains a positive pressure peak, that corresponds to the time during which the bubble expands (transmitted rarefaction), followed by a far larger negative pressure peak, that corresponds to the tie during which the bubble contracts (transmitted compression). The contraction then was followed by two cycles of expansion, where one of these cycles may be an elastic bounce.

Figure 2A:
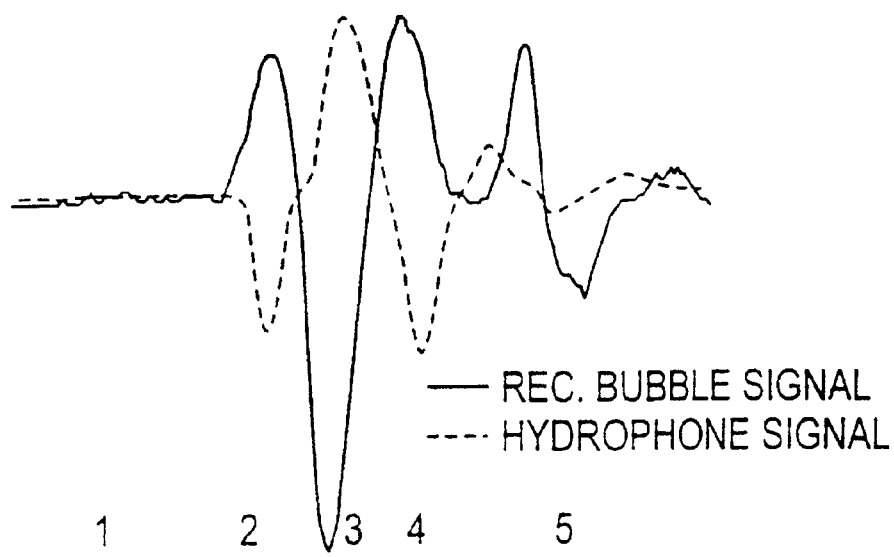
FIG. 2 compares the graph of FIG. 1 with bubble size.
Figure 2B:
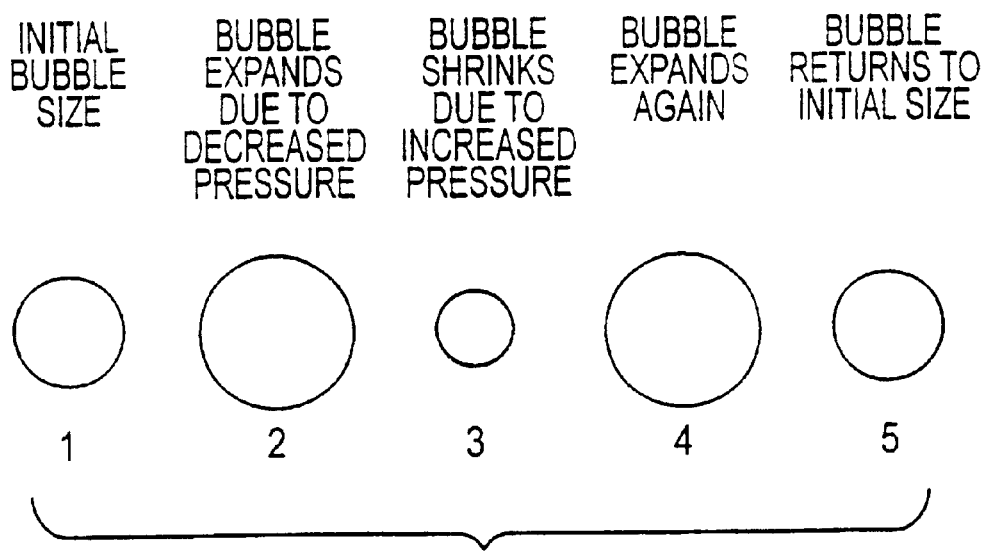

FIG. 2 shows correspondence between hydrophone and echo signals, and the changes in the bubble diameter, 2 MHz center frequency of transmission. FIGS. 2a and 2b detail the correspondence between the transmitted pressure, echo amplitude and bubble radius.

Figure 3:
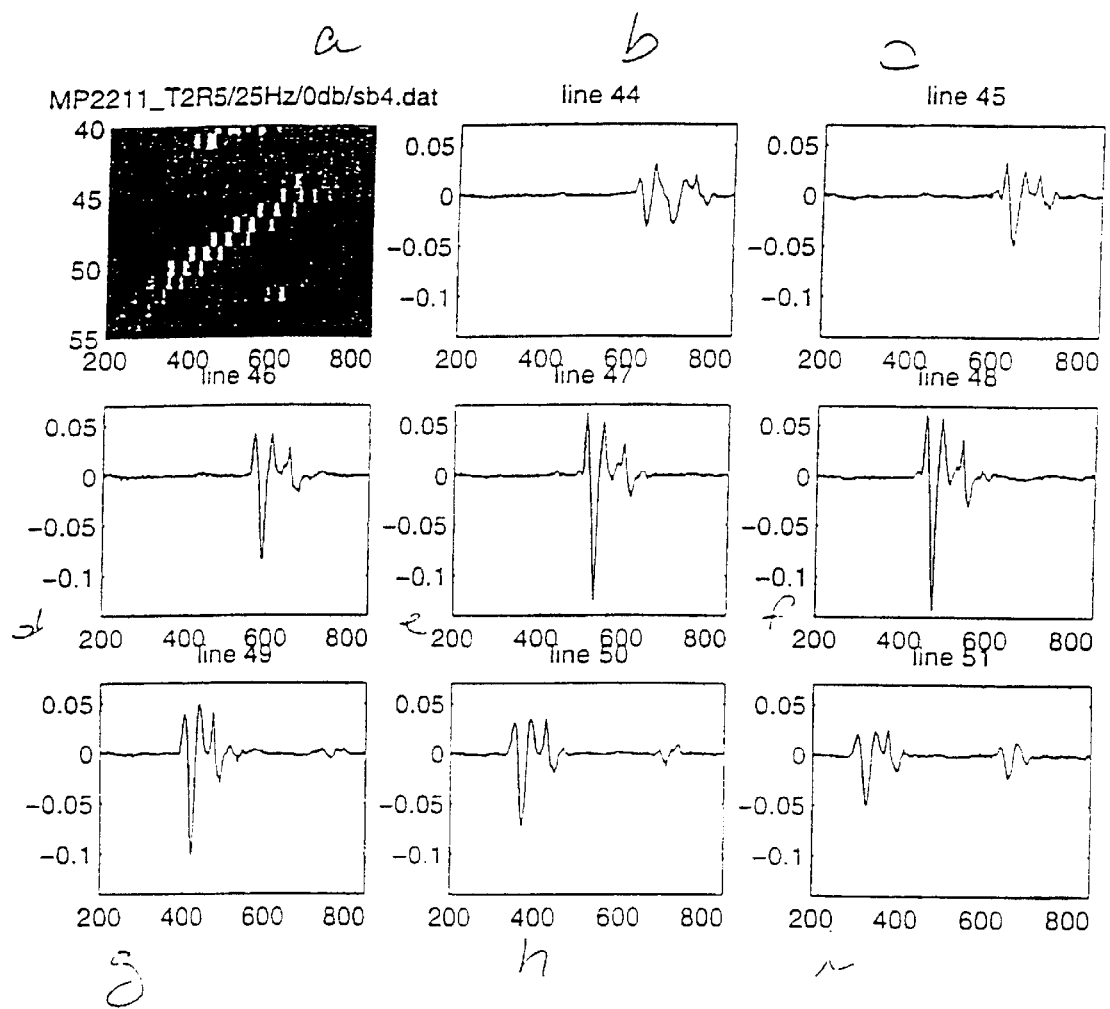
FIG. 3 graphically depicts M-mode and A-lines corresponding to a bubble.

FIG. 3 shows M-mode and A-lines corresponding to a bubble moving across the transducer beam, 2 MHz center frequency of transmission. FIG. 3a is a small M-mode image with depth shown on the horizontal axis and the pulse index shown on the vertical axis. The bubble entered the beam at depth 800 during pulse 44. The echo amplitude then increased substantially as the bubble entered the center of the beam, which corresponds to approximately depth 500. The intensity of the ultrasonic pulse that hits the bubble increased until the bubble reached the center of the beam, and then decreased again. As the pulse intensity increased, the echo developed and assumed the signature of FIGS. 1–2 in FIG. 3f.

Figure 4:
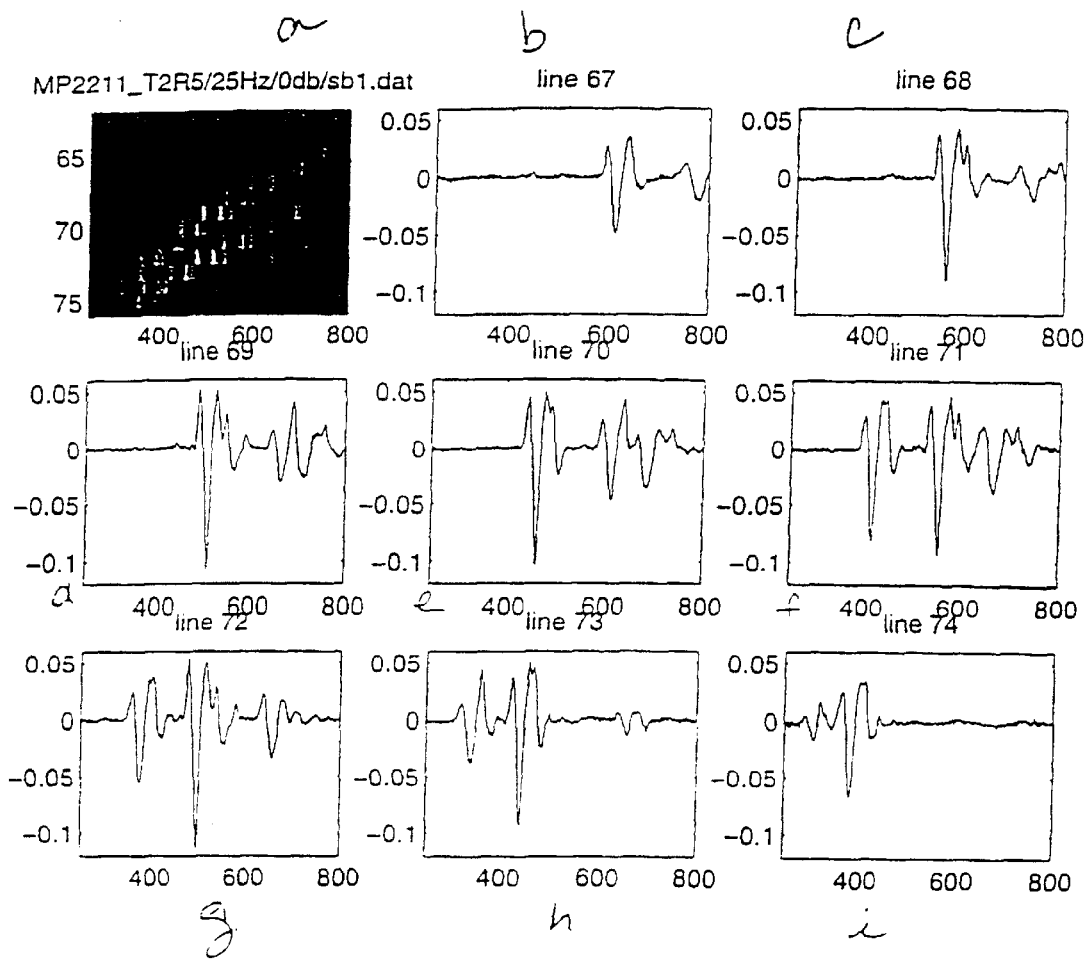
FIG. 4 graphically depicts M-mode and A-lines corresponding to two bubbles.

FIG. 4 shows M-mode and A-lines corresponding to two bubbles moving across the transducer beam, 2 MHz center frequency of transmission. Two separate tracks are visualized in the M-mode image, corresponding to two bubbles moving across the beam. The first echo from the first of these bubbles is seen in FIG. 4b, beginning as a linear echo. As the bubble moved across the beam, the echo signature changed, again assuming the signature presented in FIGS. 1–2. In FIG. 4f, a second bubble appeared at the deeper depth of approximately 700, in addition to the bubble from above which was at depth 500. As this second bubble moved across the beam (in FIG. 4g it is located in the center of the beam), the echo signature again takes the form shown in FIGS. 1–2.

Figure 5:
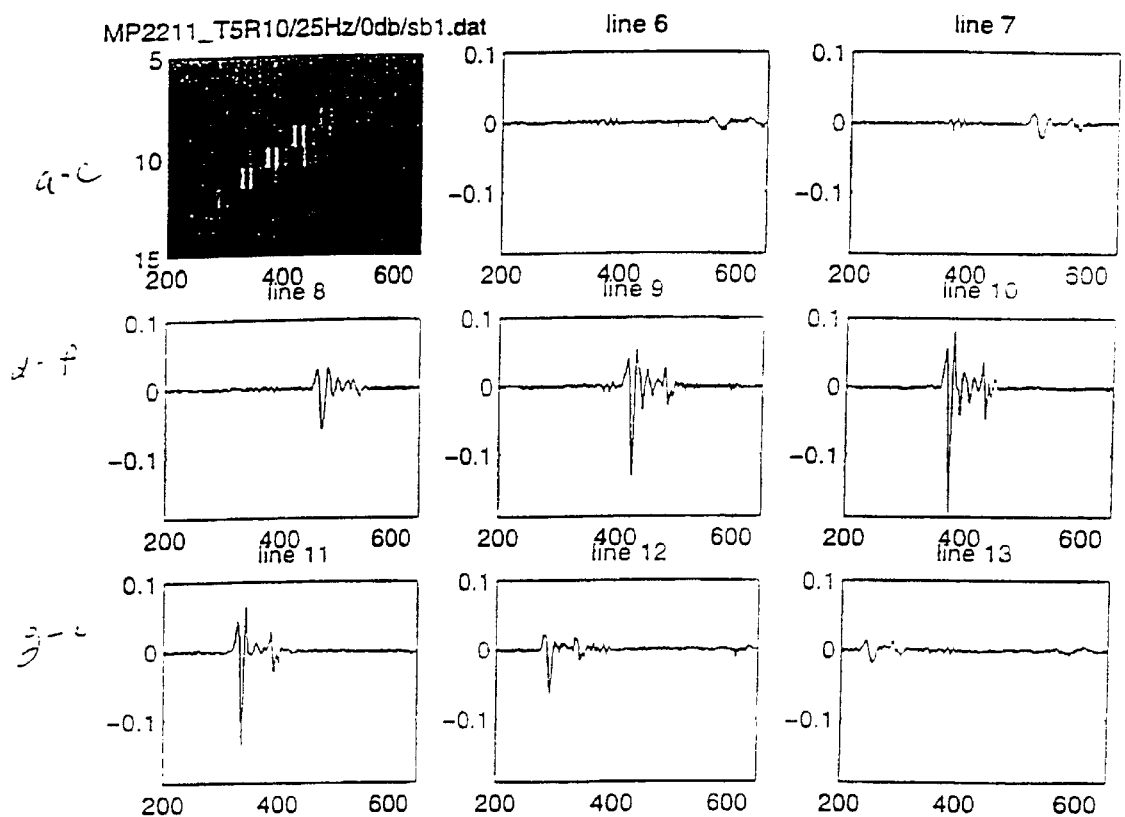
FIG. 5 graphically depicts M-mode and A-lines corresponding to another pair of bubbles.
Figure 6B:
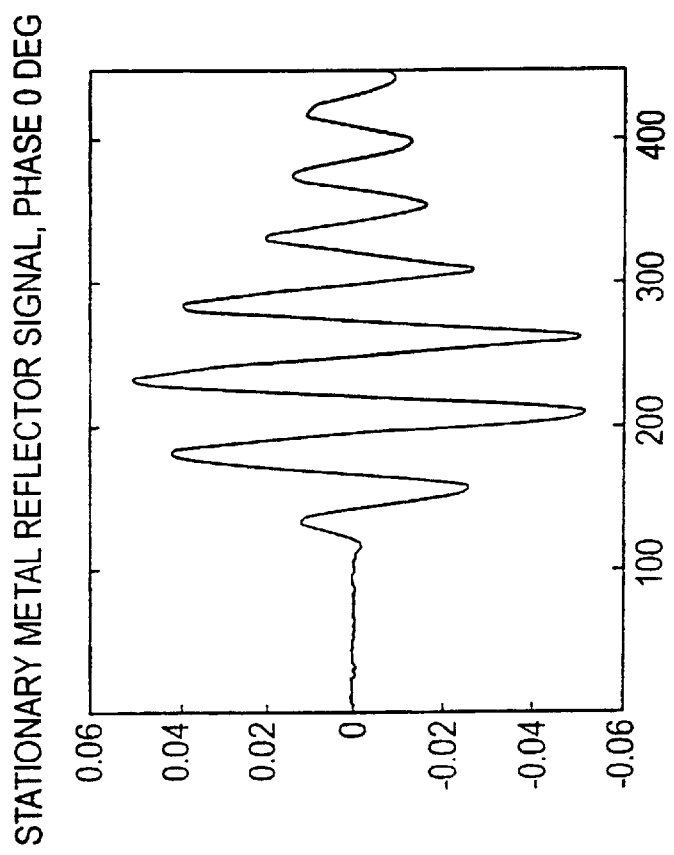
FIG. 6 graphically depicts the effect of change in a transmitted signal.
Figure 6A:
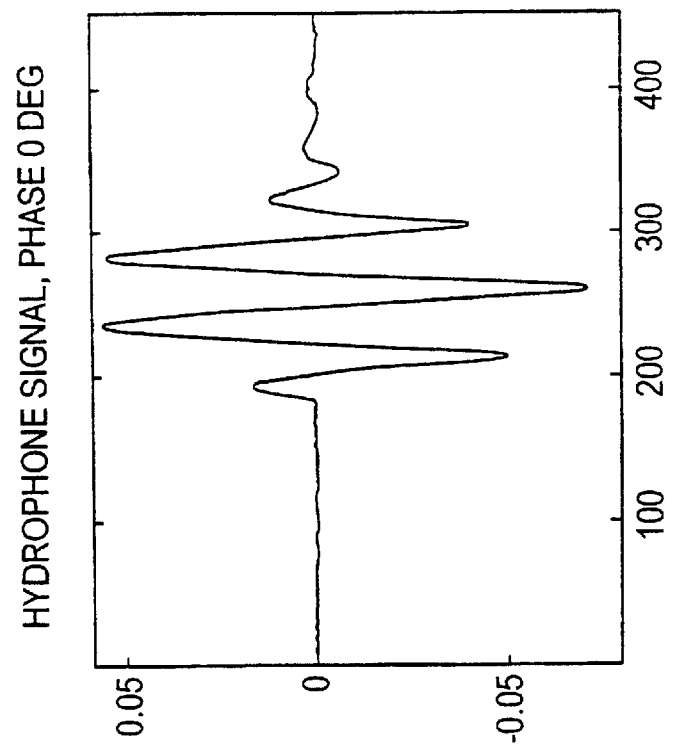
Figure 6D:
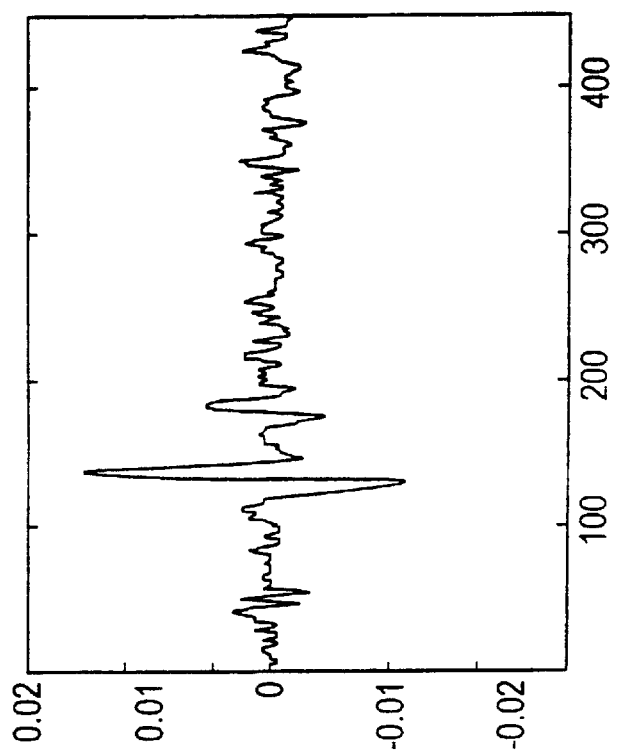
Figure 6C:
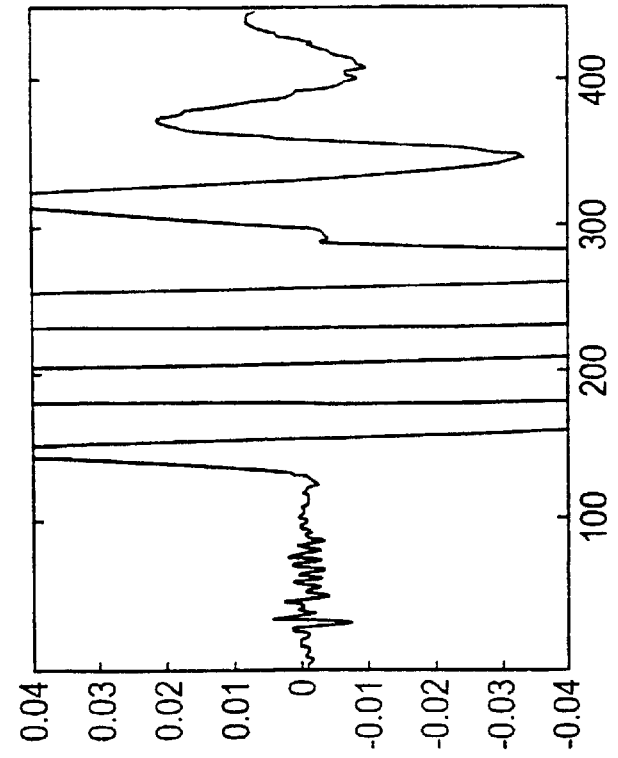

FIG. 5 shows M-mode and A-lines corresponding to two bubbles moving across the transducer beam, 5 MHz center frequency of transmission. The bubble shown in this figure has a 5 MHz resonance frequency. Again the bubble entered from a deeper depth, in this case near the index 600. As the bubble moved across the transducer beam, the echo intensity increased and a similar signature to that shown in FIGS. 1–2 was produced. The echo phase again initially corresponds to bubble expansion (a positive voltage), followed by a large negative voltage corresponding to the bubble elastically bouncing in radius. This repeatable signature was recognized and the information combined with that gained from 2 MHz transmission.

FIG. 6 shows the effect of change in the transmitted signal. In this case we transmitted a waveform with three complete cycles of compression followed by rarefaction (compression-rarefaction-compression-rarefaction-compression-rarefaction), thus different than that shown in FIG. 7. The echo received at this lower intensity was slightly different in shape than that of FIGS. 1–2, however we examined the effect of a phase shift for this case. In FIG. 6a, we observed the hydrophone echo for this transmitted signal, which contained the three cycles which were amplitude modulated. In FIG. 6b, we show the echo from a stationary metal reflector and note that the phase of the echo was identical to the phase of the transmitted signal as expected. In FIG. 6c, we show the echo from a large air bubble (>200 microns) moving through our flowing system and again note that the phase was identical to phase of the transmitted signal. FIG. 6d, we show the echo from a single contrast bubble, which is noted to be identical in phase to the transmitted signal. The bubble echo also has a trailing cycle consistently produced by this particular excitation pulse. The contrast agent echo has three positive peaks with the center peak being far larger.

Figures 7A, 7B:
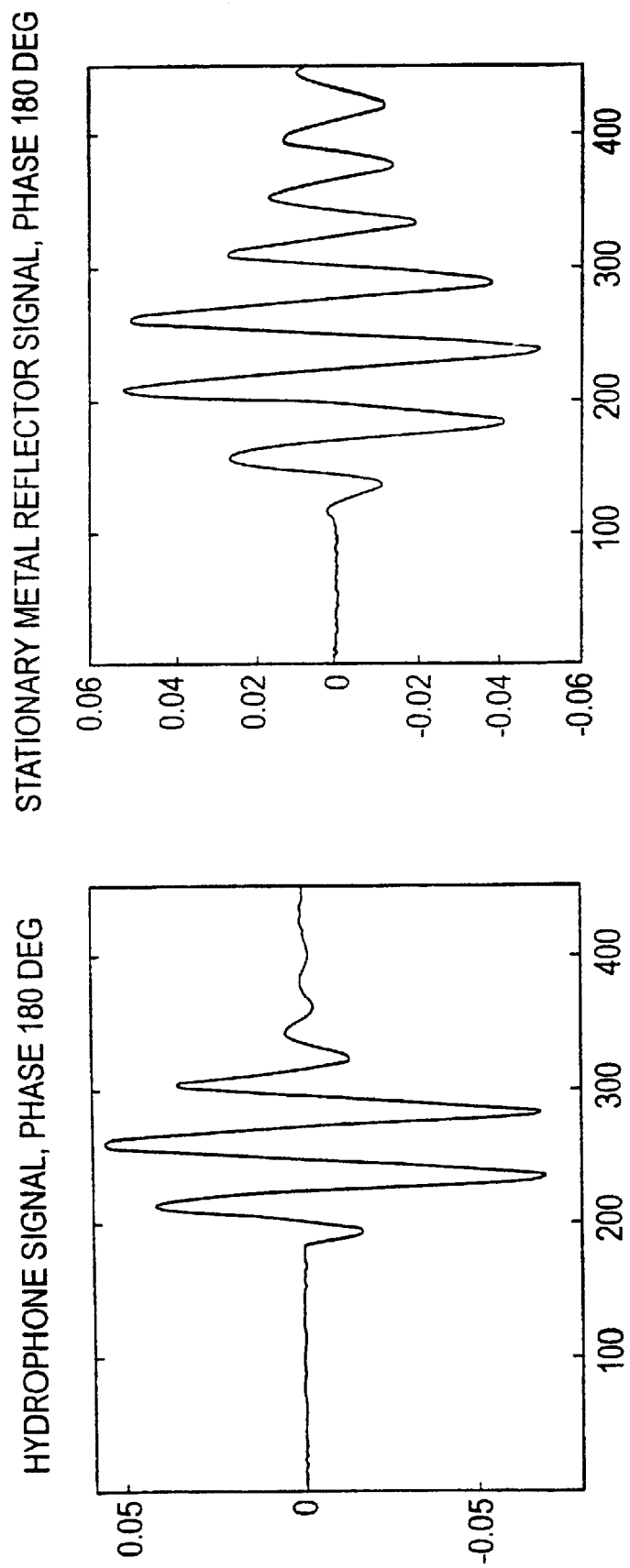
FIG. 7 graphically depicts the effect of a phase shift in a transmitted signal.
Figure 7D:
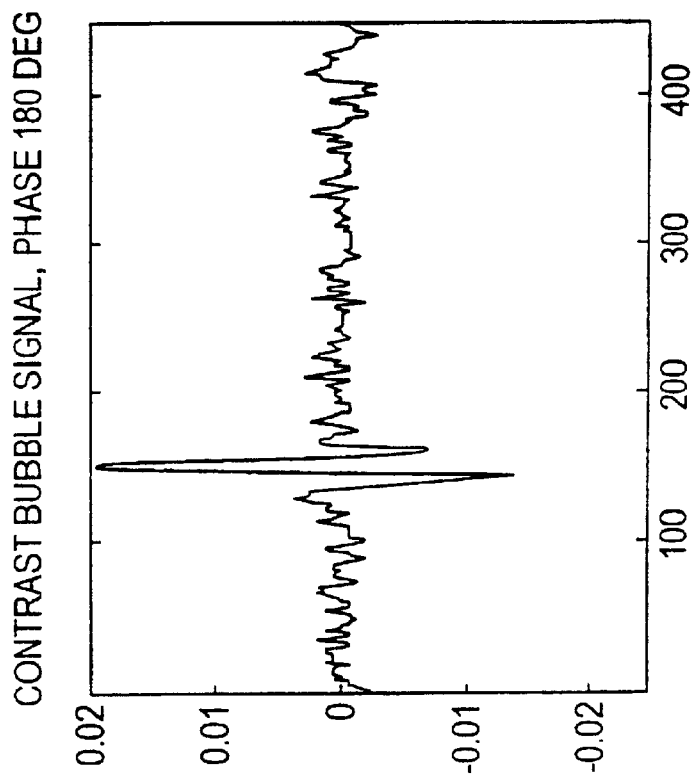
Figure 7C:
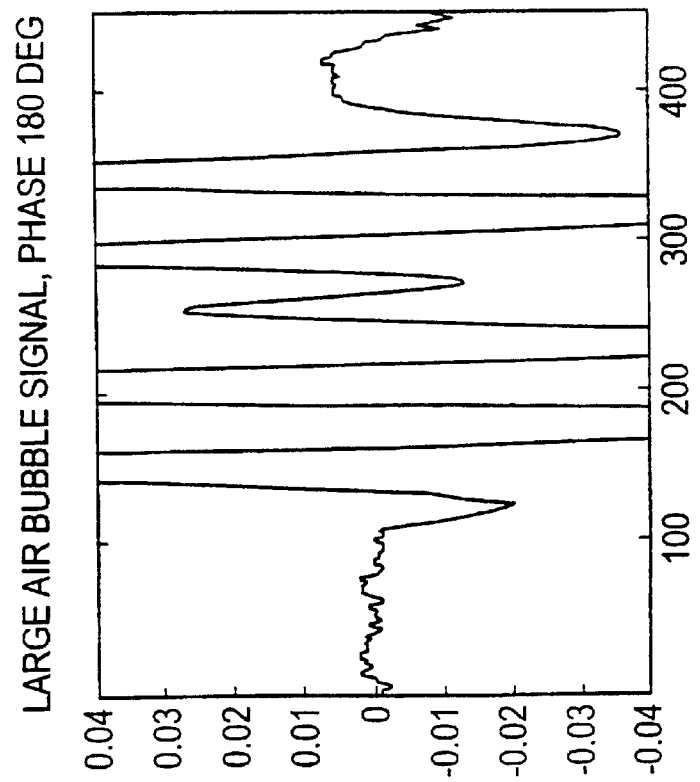

FIG. 7 shows the effect of a phase shift in the transmitted signal. In this case we transmitted a waveform with two significant cycles of compression followed by rarefaction, (compression-rarefaction-compression-rarefaction) thus different than that shown in FIG. 6. Note that there are only two significant negative half cycles. In FIG. 7a, we observed the hydrophone echo for this case. In FIG. 7b, we show the echo from a stationary metal reflector, and noted that the phase of the echo was identical to the phase of the transmitted signal, as expected. In FIG. 7c, we show the echo from a large air bubble (>200 microns) moving through our flowing system and again note that the phase is identical to the phase of the transmitted signal. In FIG. 7d, we show the echo from a single contrast bubble, which is noted to be opposite in phase to the transmitted signal, and identical in phase to FIG. 6d. The contrast bubble's echo has two positive peaks (the first is small) that correspond to the two substantial negative peaks in the hydrophone signal. The signal is noted to be shorter than that of FIG. 6d. Thus, the echoes received from a single bubble using the two transmitted pulses shown in FIGS. 6a and 7a could be subtracted to yield the extra half cycle shown in FIG. 6.

Figure 8:
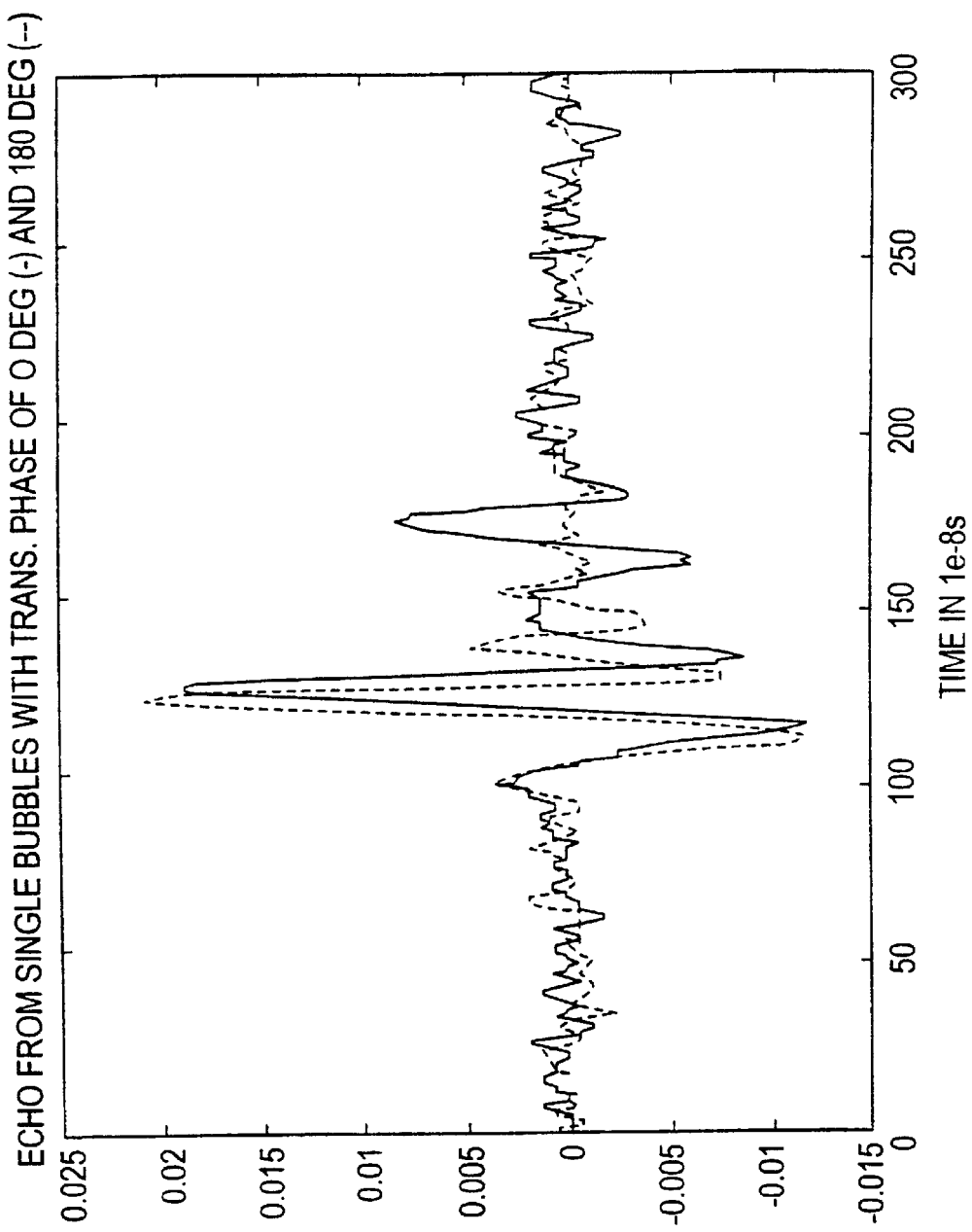
FIG. 8 graphically compares the echo shown in FIG. 6 with an echo shown in FIG. 7(d).
Figure 9:
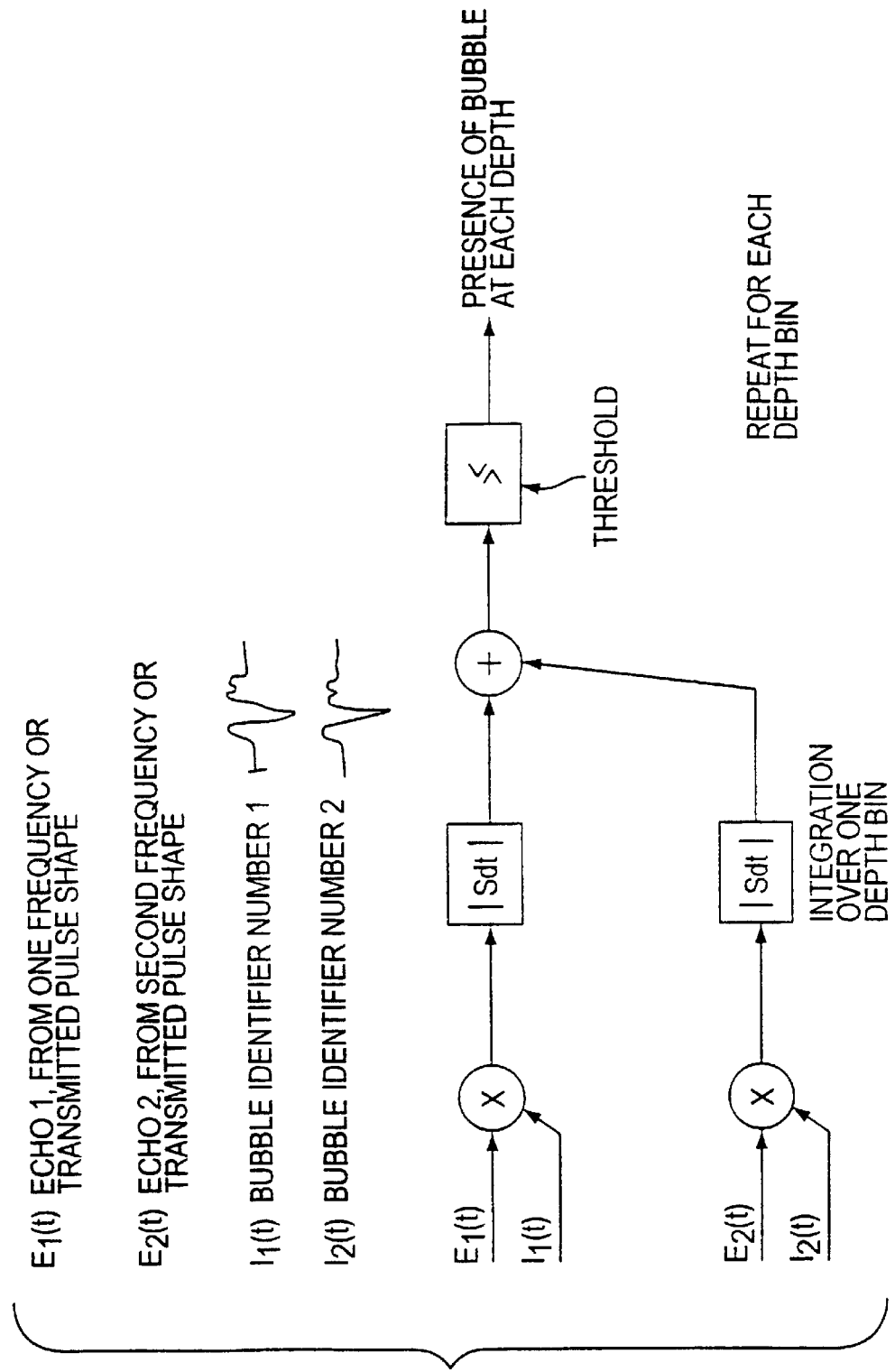
FIG. 9 is a block diagram showing a correlation receiver for transmission of two pulses.
Figure 10:
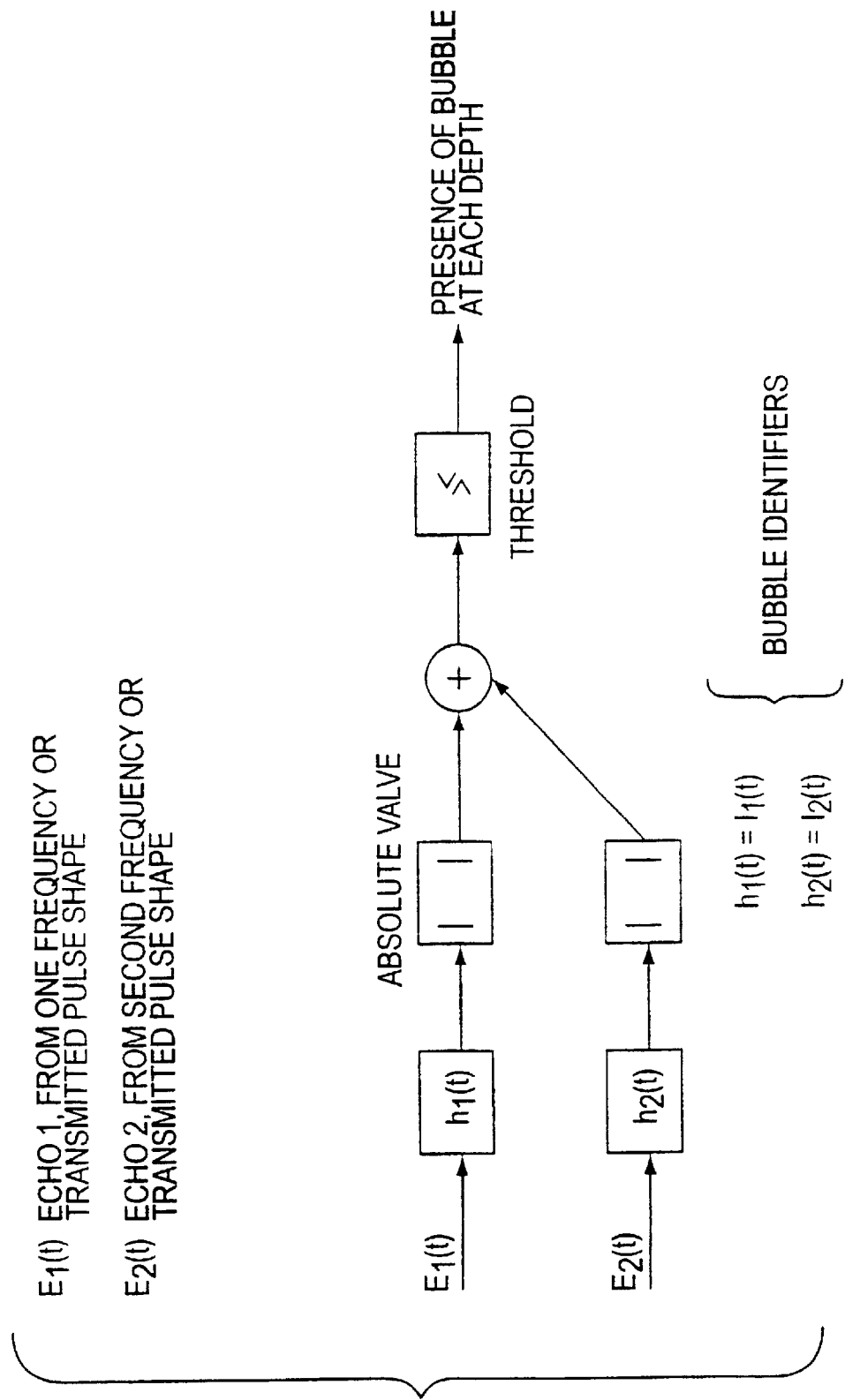
FIG. 10 is a block diagram showing a matched filter for use in accordance with the present invention.

FIG. 8 shows the two echoes shown in FIGS. 6 and 7d are overlaid to demonstrate that their phase is similar and the echo shape is also similar. These two echoes come from two different bubbles with the transmitted pulses shown in FIGS. 6 and 7.

The mean frequency of bubble echoes changes as a function of the transmitted phase, and this change is large enough to improve the differentiation of bubble and tissue echoes.

The invention is further illustrated by the following Examples, which are not intended to be limiting.

EXAMPLE 1

The order of compressional rarefactional half-cycles in the transmitted pulse affects the time and frequency domain characteristics of the received echo from an ultrasound contrast agent. These effects can be utilized to differentiate bubble and tissue echoes.

The method allows both optical and acoustical observation of contrast agent microbubbles. The test system utilized two perpendicular transducers mutually focussed on 200-micron diameter cellulose phantom tubing that was at a 45° angle to the two transducers. One transducer was used to transmit pulses at a center frequency of 2.25 MHz (Panametrics™ V305) and the other received the signals scattered from the bubbles in the vessel using a center frequency of 5 MHz (Panametrics™ V309). The phantom also was coupled to a microscope for optical viewing of the microbubbles. The transmitted pulses were generated using an arbitrary waveform generator (Tektronics™ AWG2021) and then amplified using a RF power amplifier (ENI™ 325LA). The bubble echoes were received using a broadband receiver (Ritec™ BR-640). The peak negative transmitted pressure was approximately 700 kPa. These experiments utilized a very low concentration of a contrast agent suspended in saline, on the order of 1 sphere/microL, and our experimental system with small diameter tubing produced a contrast-filled sample volume of approximately 0.04 microL. Similar results have been obtained with several agents, but the results presented here are obtained using an experimental agent that has a lipid shell and a perfluorohydrocarbon core.

The transducer was excited by single cycle pulses with a phase of 0° (compressional half-cycle followed by rarefactional half-cycle) and a phase of 180° (rarefactional half-cycle followed by compressional half-cycle). The echoes received from single bubbles were recorded from more than 200 transmissions for each phase. The received echoes from pairs of transmitted pulses separated by approximately 3 microseconds (as shown in FIG. 1) were also recorded. Approximately 50 echoes were evaluated for each of the following three transmission sequences; both pulses with 0° phase, the 0° phase followed by 180° phase, and 180° phase followed by 0° phase. Using this data, both time and frequency domain characteristics were evaluated. We also compared echo recordings with optical images of variations in the bubble radius during insonation of microbubbles tethered to a polystyrene plate.

The effect of transmitted phase on frequency spectrum and time domain envelope of bubble echoes was as follows. The mean frequency of the bubble echo was lower when the 0° case was transmitted. Specifically, when the 0° case was transmitted, a mean frequency of 3.9 MHz was observed, while a mean frequency of 4.3 MHz was observed when the transmitted pulse had a phase of 180°. In addition, the 0° case often resulted in a longer time domain envelope.

Table 1, below, shows that the time interval between the first major rarefactional peaks of the two received echoes corresponds to the time interval between transmitted rarefactional peaks. The mean received time intervals are summarized, together with the time intervals for the transmitted pulses as measured by a hydrophone. The results show a dependence of the received echo timing on rarefactional half-cycles. Specifically, if the time between transmitted rarefactional half-cycles was decreased, as in the 0°–180° phase case, the time measured between the received rarefactional peaks decreased proportionally. The results indicate that the significant portion of the bubble echo coincided with the first major rarefactional half cycle of the transmitted signal.

TABLE 1

Time interval between the first major rarefactional peaks in each pulse pair on transmission and reception

| Transmitted phase combination | Transmission: Time between first major rarefactional peaks in a pulse pair (microseconds) | Received echoes: time between first major rarefactional peaks in a pulse pair (microseconds) |
|---|---|---|
| 0–0 | 2.95 | 2.94 |
| 0–180 | 2.72 | 2.70 |
| 180–0 | 3.16 | 3.20 |

FIGS. 19a, 19b and 19c show transmitted signals used to excite the wideband transducer. FIG. 19a shows two identical pulses with compression followed by rarefaction. FIG. 19b shows pulse pair with compression followed by rarefaction in the first pulse and rarefaction followed by compression in the second pulse. FIG. 19c shows pulse pair with rarefaction followed by compression in the first pulse and compression followed by rarefaction in the second pulse.

Figure 20A:
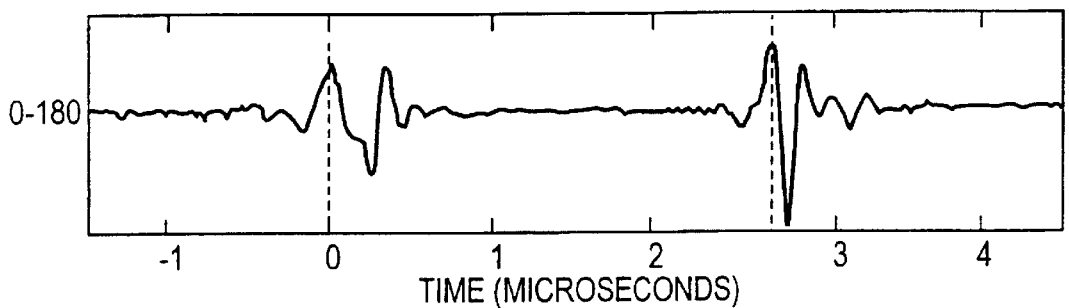
FIGS. 20a, 20b, 20c and 20d graphically depict sets of received echoes from individual lipid-shelled bubbles having a perfluorohydrocarbon core.
Figure 20B:
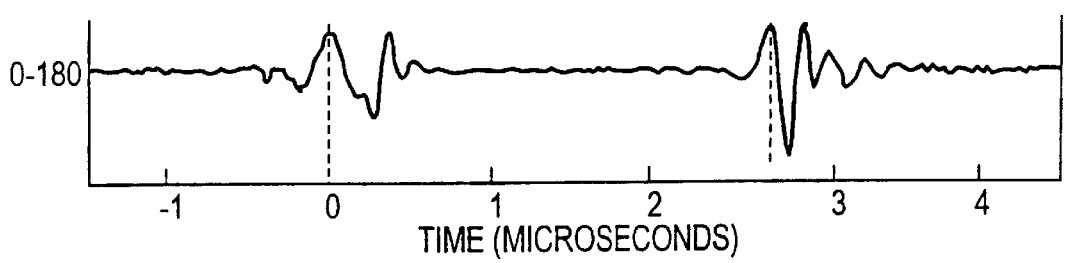
Figure 20C:
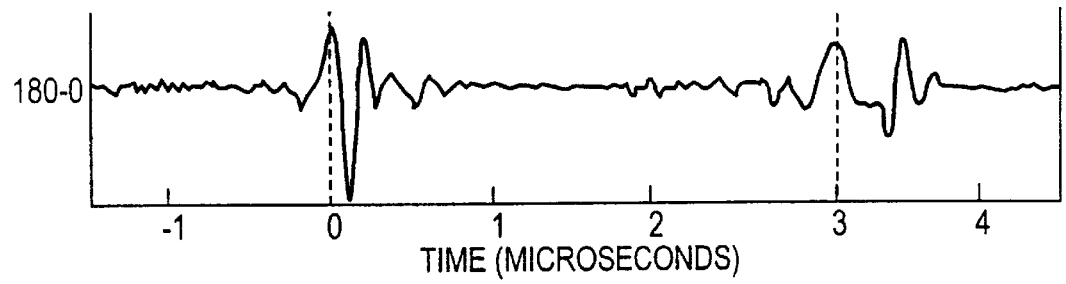
Figure 20D:
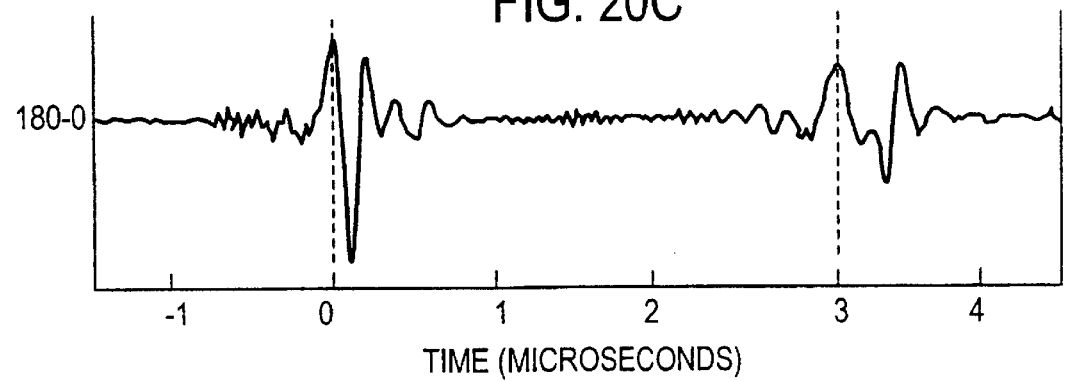

FIGS. 20a, 20b, 20c and 20d show received echoes from individual bubbles demonstrating the results of changes in the transmitted phase. FIGS. 20a and 20b are examples of the 0°–180° transmitted phase combination. FIGS. 20c and 20d are examples of the 180°–0° transmitted phase combination. The first compressional peak has been aligned between the two cases, in order to facilitate a comparison of the echo timing.

In FIG. 20, echoes from individual bubbles insonified by pairs of pulses are shown, including two echoes received following the 180–0° transmitted phase combination and two echoes received following the 0°–180° transmitted phase combination. Note that the echoes resulting from each transmitted phase were similar in all cases. It is thus demonstrated that for very short transmissions, the time domain envelope from a single bubble echo is predictable. This indicates that bubbles can be recognized by correlating received echoes with a bubble echo prototype.

Characteristics of bubble echoes, including the mean frequency, duration and time domain signature, change with the transmitted signal phase and demonstrate a high correlation between successive echoes. Transmission of several signal phases can be utilized to identify bubbles in vivo.

EXAMPLE 2

Measurements have been made for several contrast agents, both for those with an albumin shell and those with a lipid shell, demonstrating that the mean frequency of bubble echoes changes as a function of the transmitted phase, and that this change is large enough to improve the differentiation of bubble and tissue echoes. However, the mean frequencies are slightly different for albumin shell and lipid shell contrast agents, as shown in Table 2.

TABLE 2

|  | Albumin Shell | | Lipid Shell | |
|---|---|---|---|---|
| Phase of transmission | 0 | 180 | 0 | 180 |
| # of bubbles | 72 | 72 | 75 | 75 |
| mean frequency (MHz) | 3.45 | 3.98 | 3.74 | 4.42 |

Filtering the bubbles to achieve a restricted distribution greatly decreases the standard deviation of the estimate of mean frequency.

In order to use the above results for signal processing, the following steps are used. Tissue echo is rejected through use of a wall filter or through elimination of frequencies near the fundamental frequency utilizing a high pass filter. The mean frequency is estimated to identify presence of a bubble. The mean frequency is calculated as a function of depth for the 0° and 180° pulses, and a significant shift in this frequency indicates the presence of a bubble or bubbles.

Figure 15:
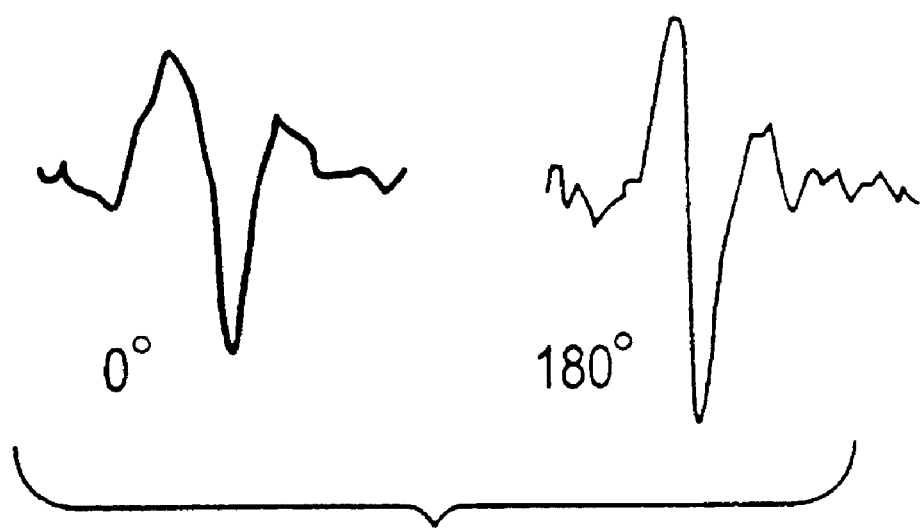
FIG. 15 graphically depicts scattered echoes from a contrast agent bubble with a 0° and 180° phase of transmission.

FIG. 15 shows scattered echoes from a contrast agent bubble with a 0° and 180° phase of transmission. The phase of the transmitted signal has been inverted, but the received echo is not inverted. The mean frequency is different between the two echoes. The mean frequency is higher for the 180° transmission, as observed by the shorter pulse.

FIGS. 16a and 16b show Hydrophone recording of the transmitted signals in the 0° and 180° cases. Note that they are inverted. Recorded echoes are shown from contrast agent bubbles for the two cases. Note that they have the envelope shown in FIG. 16, but that the echo from the 180° transmission is delayed such that it occurs during the rarefactional half cycle in each case.

FIGS. 17a and 17b show two sets of recordings of the echoes from 4 pulses separated by 1.25 microseconds. Echoes are generated by a single albumin bubble. The transmission of pulses alternated between 0° and 180°, and the transmitted pulses were evenly spaced. Note that the received echoes alternate between the two delays (the spacing of echoes is uneven- and corresponds to the timing of transmitted rarefaction). The echoes also alternate between the two mean frequencies associated with 0° and 180°. Note also that the echo strength grows between successive pulses, as the albumin shell weakens.

FIGS. 18a and 18b show two sets of recordings of the echoes from 4 pulses separated by 1.25 microseconds. Echoes were generated by a single lipid bubble. The transmission of pulses alternated between 0° and 180°, and the transmitted pulses were evenly spaced. Note that the received echoes alternate between the two delays (the spacing of echoes is uneven—and corresponds to the timing of transmitted rarefaction). The echoes also alternate between the two mean frequencies associated with 0° and 180°. Note also that the echo strength does not grow between successive pulses for the lipid-shelled bubble.

FIGS. 17 and 18 show the consistency of the results, and indicate that two different agents could be injected and their echoes differentiated using these properties.

As indicated above the present invention can provide many advantages over the prior art.

With respect to detection of breast cancer, one immediate clinical benefit from this invention is a new ability to guide needle biopsy in all patients, not simply those with a hypoechoic solid mass. Even patients with cancerous tumors, without a detectable solid mass, demonstrate changes in local vascularity. More generally, this invention is a significant improvement in the positive predictive value of ultrasonic evaluation of an identified mass.

This invention also has implications for study of cardiovascular disease (CVD) since it is applicable for the evaluation of myocardial perfusion.

What is claimed is:

1. A method of identifying gaseous bubbles in a liquid, comprising:
   a) introducing an ultrasound contrast agent into a liquid so as to form gaseous bubbles in said liquid;
   b) directing a first ultrasound pulse centered at a first frequency onto said bubbles so as to cause said bubbles to undergo a first oscillating size change and produce a first oscillating echo signal corresponding to the first oscillating size change of the bubbles;
   c) detecting the first oscillating echo signal produced by said bubbles;
   d) identifying said bubbles based upon the detected first echo signal;
   e) directing a second ultrasound pulse centered at a second frequency different from said first frequency onto said bubbles, so as to cause said bubbles to undergo a second oscillating size change and produce a second oscillating echo signal corresponding to the second oscillating size change of the bubbles;
   f) detecting the second oscillating echo signal produced by said bubbles; and
   g) further identifying said bubbles based upon the detected second echo signal.

2. The composition of claim 1, wherein said steps further include the step of comparing the first echo signal with a first reference echo signal indicative of said bubbles, so as to identify said bubbles.

3. The composition of claim 1 wherein said first frequency is about a resonant frequency of said bubbles.

4. The composition of claim 3 wherein the resonance frequency is about 1.5–5 MHZ.

5. The composition of claim 1 wherein said first pulse has a duration that is about equal to or less than three cycles of a center frequency of the first pulse.

6. The composition of claim 5 wherein said first pulse has a duration of about 1.5 cycles of a center frequency of the first pulse.

7. The method of claim 1, further including the steps of comparing the first and second echo signals respectively with first and second reference echo signals indicative of said bubbles, so as to identify said bubbles.

8. The method of claim 1 wherein said second frequency is within about 5 MHz of the first frequency.

9. The composition of claim 8 wherein said second frequency is within about 4 MHZ above said first frequency.

10. The composition of claim 8 wherein said second frequency is within about 3 MHZ below said first frequency.

11. The method of claim 1 wherein there is a substantial difference between the first and second echo signals.

12. The composition of claim 1 wherein said bubbles are identified by detecting a frequency shift of said first echo signal.

13. The method of claim 1 wherein said bubbles are further identified by detecting a frequency shift of said second echo signal.

14. A method of identifying gaseous bubbles in a liquid, comprising:
   a) introducing an ultrasound contrast agent into a liquid so as to form gaseous bubbles in said liquid;
   b) directing a first ultrasound pulse centered at a first frequency onto said bubbles so as to cause said bubbles to undergo a first oscillating size change and produce a first oscillating echo signal corresponding to the first oscillating size change of the bubbles;
   c) detecting the first oscillating echo signal produced by said bubbles;
   d) identifying said bubbles based upon the detected first echo signal;
   e) directing a further ultrasound pulse centered at said first frequency onto said bubbles, so as to cause said bubbles to undergo a further oscillating size change and produce a further oscillating echo signal corresponding to the further oscillating size change of the bubbles;

f) detecting the further oscillating echo signal produced by said bubbles; and g) further identifying said bubbles based upon the detected further echo signal.

15. The composition of claim 14, wherein said steps further include the step of comparing the first and further echo signals, so as to identify said bubbles.

16. The composition of claim 14 wherein said further ultrasound pulse differs from said first ultrasound pulse in a characteristic selected from the group consisting of phase, amplitude and a combination thereof.

17. The composition of claim 14 wherein said steps further include the steps of:

directing a plurality of the further ultrasound pulses onto said bubbles, so as to produce a plurality of the further oscillating echo signals;

detecting the plurality of further oscillating echo signals produced by said bubbles; and further identifying said bubbles based upon the detected further echo signals.

18. The composition of claim 17 wherein said bubbles are further identified by detecting a shift in frequency of said further echo signals.

19. The composition of claim 17, wherein said steps further include the step of comparing the first and further echo signals, so as to identify said bubbles.

20. The composition of claim 19 wherein said plurality of further ultrasound pulse s differ from said first ultrasound pulse by a shift in center frequency.

21. The composition of claim 19 wherein said plurality of further ultrasound pulses differ from said first ultrasound pulse in a characteristic selected from the group consisting of phase, amplitude and a combination thereof.

22. The composition of claim 14 wherein said bubbles are further identified by detecting a shift in frequency of said further echo signal.

23. The composition of claim 14 wherein said further ultrasound pulse differs from said first ultrasound pulse by a shift in center frequency.

24. A method of mapping tissue in a patient, comprising:

a) introducing an ultrasound contrast agent into a body liquid present in a patient's vascular system so as to form gaseous bubbles in said liquid;

b) directing a first ultrasound pulse centered at a first frequency onto said bubbles so as to cause said bubbles to undergo a first oscillating size change and produce a first oscillating echo signal corresponding to the first oscillating size change of the bubbles;

c) detecting the first oscillating echo signal produced by said bubbles;

d) identifying said bubbles based upon the detected first echo signal;

e) directing a second ultrasound pulse centered at a second frequency different from said first frequency onto said bubbles, so as to cause said bubbles to undergo a second oscillating size change and produce a second oscillating echo signal corresponding to the second oscillating size change of the bubbles;

f) detecting the second oscillating echo signal produced by said bubbles;

g) further identifying said bubbles based upon the detected second echo signal; and h) mapping tissue of said patient based upon identification of said bubbles.

25. The composition of claim 24, wherein said steps further include the step of comparing the first echo signal with a first reference echo signal indicative of said bubbles, so as to identify said bubbles.

26. The method of claim 24, further including the steps of comparing the first and second echo signals respectively with first and second reference echo signals indicative of said bubbles, so as to identify said bubbles.

27. The composition of claim 24 wherein said bubbles are identified by detecting a shift in frequency of said first echo signal.

28. The method of claim 24 wherein said bubbles are further identified by detecting a shift in frequency of said second echo signal.

29. A method of mapping tissue in a patient, comprising:

a) introducing an ultrasound contrast agent into a body liquid present in a patient's vascular system so as to form gaseous bubbles in said liquid;

b) directing a first ultrasound pulse centered at a first frequency onto said bubbles so as to cause said bubbles to undergo a first oscillating size change and produce a first oscillating echo signal corresponding to the first oscillating size change of the bubbles;

c) detecting the first oscillating echo signal produced by said bubbles;

d) identifying said bubbles based upon the detected first echo signal;

e) directing a further ultrasound pulse centered at said first frequency onto said bubbles, so as to cause said bubbles to undergo a further oscillating size change and produce a further oscillating echo signal corresponding to the further oscillating size change of the bubbles;

f) detecting the further oscillating echo signal produced by said bubbles; and g) further identifying said bubbles based upon the detected further echo signal.

30. The composition of claim 29, wherein said steps further include the step of comparing the first and further echo signals, so as to identify said bubbles.

31. The composition of claim 29 wherein said further ultrasound pulse differs from said first ultrasound pulse in a characteristic selected from the group consisting of phase, amplitude and a combination thereof.

32. The composition of claim 29 wherein said steps further include the steps of:

directing a plurality of the further ultrasound pulses onto said bubbles, so as to produce a plurality of the further oscillating echo signals;

detecting the plurality of further oscillating echo signals produced by said bubbles; and further identifying said bubbles based upon the detected further echo signals.

33. The composition of claim 32 wherein said bubbles are further identified by detecting a shift in frequency of said further echo signals.

34. The composition of claim 32, wherein said steps further include the step of comparing the first and further echo signals, so as to identify said bubbles.

35. The composition of claim 34 wherein said plurality of further ultrasound pulses differ from said first ultrasound pulse in a characteristic selected from the group consisting of phase, amplitude and a combination thereof.

36. The composition of claim 29 wherein said bubbles are further identified by detecting a shift in frequency of said further echo signal.

37. The composition of claim 34 wherein said plurality of further ultrasound pulses differ from said first ultrasound pulse by a shift in center frequency.

38. The composition of claim 29 wherein said further ultrasound pulse differs from said first ultrasound pulse by a shift in center frequency.

* * * * *

UNITED STATES PATENT AND TRADEMARK OFFICE
CERTIFICATE OF CORRECTION

PATENT NO. : 6,371,917 B1
DATED : April 16, 2002
INVENTOR(S) : Katherine W. Ferrara et al.

It is certified that error appears in the above-identified patent and that said Letters Patent is hereby corrected as shown below:

<u>Title page,</u>
Item [86], PCT No. replace "PCT/US98/87182" with -- PCT/US98/18245 --.

Signed and Sealed this

Fourth Day of February, 2003

JAMES E. ROGAN
*Director of the United States Patent and Trademark Office*